US012136481B2

(12) United States Patent
Baker et al.

(10) Patent No.: US 12,136,481 B2
(45) Date of Patent: Nov. 5, 2024

(54) MEDICAL IMAGING CHARACTERISTIC DETECTION, WORKFLOWS, AND AI MODEL MANAGEMENT

(71) Applicant: Virtual Radiologic Corporation, Minneapolis, MN (US)

(72) Inventors: Brian M Baker, Minnetonka, MN (US); Wade J. Steigauf, Bloomington, MN (US); Benjamin Strong, Tucson, AZ (US); Robert Harris, Maple Grove, MN (US); Jerry Lohr, Burnsville, MN (US); Steven Towey, Eden Prairie, MN (US)

(73) Assignee: Virtual Radiologic Corporation, Minneapolis, MN (US)

( * ) Notice: Subject to any disclaimer, the term of this patent is extended or adjusted under 35 U.S.C. 154(b) by 1171 days.

(21) Appl. No.: 16/909,570

(22) Filed: Jun. 23, 2020

(65) Prior Publication Data
US 2021/0398650 A1 Dec. 23, 2021

(51) Int. Cl.
*G16H 30/20* (2018.01)
*A61B 6/00* (2006.01)
*G06N 3/08* (2023.01)
*G16H 30/40* (2018.01)
*G16H 40/63* (2018.01)
(Continued)

(52) U.S. Cl.
CPC .............. *G16H 30/20* (2018.01); *A61B 6/52* (2013.01); *A61B 6/5294* (2013.01); *G06N 3/08* (2013.01); *G16H 30/40* (2018.01); *G16H 40/63* (2018.01); *G16H 40/67* (2018.01); *G16H 50/20* (2018.01);
(Continued)

(58) Field of Classification Search
CPC ........ G16H 30/20; G16H 30/40; G16H 40/63; G16H 40/67; G16H 50/20; G16H 50/70; G16H 70/60; G16H 80/00; A61B 6/52; A61B 6/5294; G06N 3/08; G06N 3/045
See application file for complete search history.

(56) References Cited

U.S. PATENT DOCUMENTS 7,970,188 B2 6/2011 Mahesh et al.
9,846,938 B2 12/2017 Steigauf et al.
(Continued)

OTHER PUBLICATIONS

"Radiology AI", vRad, MEDNAX Radiology Solutions, [Online] Retrieved from the Internet: <URL: https://info.vrad.com/radai#werehelpingpatientstoday>, (Retrieved on Jul. 1, 2020), 8 pgs.

(Continued)

*Primary Examiner* — Joseph J Dallo
(74) *Attorney, Agent, or Firm* — Schwegman Lundberg & Woessner, P.A.

(57) ABSTRACT

Systems and methods for processing electronic imaging data obtained from medical imaging procedures, with use of trained artificial intelligence (AI) models, are disclosed herein. In an example, a use of a medical evaluation workflow involving an AI model includes: obtaining image data and non-image data associated with a medical imaging study; using at least one AI model to analyze the image data, with the trained AI model being validated with a defined governance standard to identify a characteristic or particular type of characteristic; identifying the characteristic with the AI model; and communicating the identified characteristic to a location associated with evaluation of the medical imaging study.

25 Claims, 15 Drawing Sheets

(51) Int. Cl.
*G16H 40/67* (2018.01)
*G16H 50/20* (2018.01)
*G16H 50/70* (2018.01)
*G16H 70/60* (2018.01)
*G16H 80/00* (2018.01)

(52) U.S. Cl.
CPC ............. *G16H 50/70* (2018.01); *G16H 70/60* (2018.01); *G16H 80/00* (2018.01)

(56) References Cited

U.S. PATENT DOCUMENTS

| | | | |
|---|---|---|---|
| 11,430,123 B2* | 8/2022 | Kohl | .......................... G06T 7/11 |
| 11,508,061 B2* | 11/2022 | Jacob | ..................... G06N 3/047 |
| 2010/0080427 A1 | 4/2010 | Yeluri et al. | |
| 2011/0010192 A1 | 1/2011 | Backhaus et al. | |
| 2012/0243754 A1 | 9/2012 | Koff et al. | |
| 2013/0129198 A1 | 5/2013 | Sherman et al. | |
| 2013/0208955 A1 | 8/2013 | Zhao et al. | |
| 2013/0322725 A1 | 12/2013 | Enzmann et al. | |
| 2016/0015347 A1 | 1/2016 | Bregman-Amital et al. | |
| 2016/0350919 A1 | 12/2016 | Steigauf et al. | |
| 2016/0364528 A1 | 12/2016 | Reicher et al. | |
| 2018/0046761 A1 | 2/2018 | Knoplioch et al. | |
| 2018/0101645 A1 | 4/2018 | Sorenson et al. | |
| 2018/0137244 A1 | 5/2018 | Sorenson et al. | |
| 2018/0144214 A1 | 5/2018 | Hsieh et al. | |
| 2020/0364852 A1* | 11/2020 | Park | ....................... G16H 30/20 |

OTHER PUBLICATIONS

Morey, Jose M, "Ch. 11: Applications of AI Beyond Image Interpretation", in E.R. Ranscheart et al. (eds.), Artificial Intelligence in Medical Imaging, pp. 129-143, Springer Nature Switzerland AG, (2019), 15 pgs.

Nijim, Imad B, "How AI is helping ensure reporting accuracy and compliance", vRad Blog, [Online] Retrieved from the Internet: <URL: https://blog.vrad.com/how-ai-is-helping-ensure-reporting-accuracy-and-compliance>, (Jan. 3, 2020), 11 pgs.

Nijim, Imad B, "New Radiology AI Models Reduce Time to Care", vRad Blog, [Online] Retrieved from the Internet: <URL: https://blog.vrad.com/new-ai-models-reduce-time-to-care>, (Jul. 1, 2020), 13 pgs.

Nijim, Imad B, "Beyond the hype: How practical AI is enhancing radiology", vRad Blog, [Online] Retrieved from the Intenet: <URL: https://blog.vrad.com/beyond-the-hype-how-practical-ai-is-enhancing-radiology>, (Apr. 3, 2019), 11 pgs.

Obuchowski, Nancy A, "Statistical considerations for testing an AI algorithm used for prescreening lung CT images", Contemporary Clinical Trials Communications 15, Elsevier, (2019), 7 pgs.

\* cited by examiner

MEDICAL IMAGING CHARACTERISTIC DETECTION, WORKFLOWS, AND AI MODEL MANAGEMENT

TECHNICAL FIELD

Embodiments pertain to techniques and systems for processing electronic data obtained from imaging or other diagnostic and evaluative medical procedures. Some embodiments relate to data processing mechanisms for medical imaging involving the use of artificial intelligence (AI) implementations such as machine learning, deep learning, artificial neural networks, and related algorithms, to assist technologies used for evaluating medical imaging data such as in radiology, pathology, or other medical diagnostic settings.

DETAILED DESCRIPTION

Figure 1:
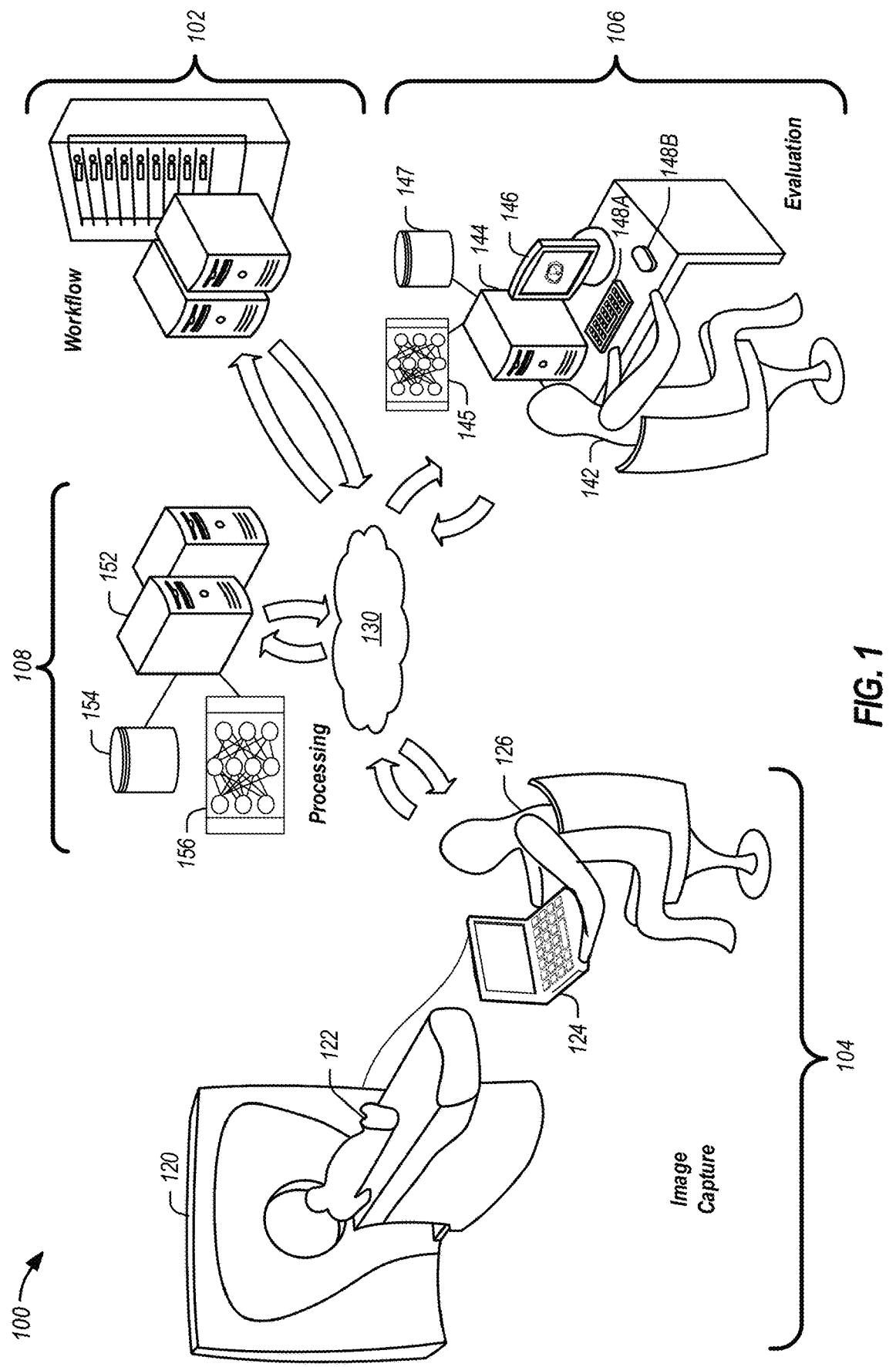
FIG. 1 illustrates a system configuration enabled for capturing, processing, directing, and evaluating medical imaging data in connection with an AI-enhanced workflow, according to an example.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure illustrates various techniques and configurations that provide the application and management of artificial intelligence (AI) technologies for a variety of aspects of medical imaging studies, whether in the specific practices of radiology or pathology, or in more general medical diagnostic, interpretative, or evaluative settings. For example, AI models (such as trained deep neural network models, trained to classify certain medical conditions or infer characteristics from images or metadata) may process medical imaging procedure data produced as part of a medical imaging study (e.g., a radiology or pathology evaluation for a particular human subject). The medical imaging procedure data may include image data captured by an imaging modality, order data (such as data indicating a request for a radiological image read), and be accompanied by other internal or external data (such as imaging metadata, health record data, prior radiology reports, etc.) related to the procedure or the subject.

As will be understood, many types and numbers of AI models may be used in an advanced medical imaging data processing workflow, for a variety of purposes. At a high level, the use of an AI model for a workflow may involve (a) using AI to infer information regarding the contents of the imaging study, such as the medical conditions presented or detected from one or more images, (b) using AI-derived information to assist handling and processing of the one or more images, or (c) some combination of these use cases. Such uses of AI model processing in a workflow is discussed in the following paragraphs as "workflow enhancement."

In an example configuration for workflow enhancement, an architecture and process for radiology workflow improvements is described, which utilizes information obtained from AI data analysis to direct operations that occur before, during, and after an imaging evaluation (e.g., radiology read). These operations may be invoked or modified as a result of detected medical findings, identified pathology conditions, or other classified conditions or inferences detected on input data by the AI model.

Additionally, it will be understood that management and coordination of AI models and model execution may be necessary to efficiently and timely analyze medical imaging data, especially due to computing resource constraints (e.g., limited bandwidth, processing power, storage) encountered with high resolution imaging data. Use and orchestration of the AI models with the following management techniques can be used to assist the medical imaging evaluation process and resulting AI processing efficiency. This coordination may occur at different areas of distributed computing platforms, such as between on-premises and remote cloud servers, and involve different or multiple AI models being selected or invoked for use. Such uses of AI model processing is discussed in the following paragraphs as "model execution management."

In an example configuration for model execution management, an architecture and process for an inference engine is described. This inference engine enables distributed execution of AI models and algorithms at different locations of a distributed computing system, such as among a cloud platform, on-premise hardware, client computing systems, and the like. This approach encompasses a variety of aspects of orchestration, governance, and distribution of execution activities of image processing and natural language processing AI models and associated algorithms, binaries, and processes.

Additionally, it will be understood that validity of a particular outcome of an AI model execution is dependent on trust and validity of the AI model itself, ensuring that the model is trained properly and can successfully reproduce outcomes within acceptable ranges of model outcomes (e.g., missed classifications, false negatives or false positives, etc.). Rather than treating the AI model as a black box, monitoring may be performed on the AI model state to determine the sensitivity and specificity of a model for given conditions or pathologies. This approach is referred to herein as AI model verification.

In an example configuration for AI model verification, an architecture and process for model verification and validation is described. This architecture and process can be used to ensure that the AI models being trained, updated, or actively used will satisfy operational criteria. Such verification can be used as part of an ongoing governance process to ensure that trained AI models are producing valid findings and classifications, even if the model is retrained or reinforced as a result of ongoing workflows. This governance may be used to change or modify current or future workflows, including to automatically remove the use of an AI model that does not successfully perform at a set sensitivity or specificity or other quality metrics.

These architectures and processes may be implemented by electronic (e.g., computer-implemented) operations in specialized software that control the operation of an overall system, through data operations at client and server computers, network communications, and related processing and messaging functions. Thus, although the present techniques relate to evaluative and diagnostic (medical) settings, a variety of technical issues involving AI model execution are addressed through improvements to technical systems used in these settings.

Each of these architecture and management examples (including the separate aspects of model execution, workflow enhancement, and model verification) may be integrated together in a number of real-world deployments. For example, consider a use case where one or more subject AI models are first provided to a model verification management process, to verify that the subject AI models can correctly identify or detect some condition from medical imaging procedure data. Then, the medical imaging procedure data can be captured and communicated to the subject AI models, which are executed on-premise or in a cloud service with model execution management. The subject AI models may be used to identify trained structures, conditions, and characteristics based on medical imaging procedure data, and implement effects within a workflow for handling the medical imaging procedure data.

In some of the following examples, reference is made to radiology medical imaging procedures (e.g., computed tomography (CT), magnetic resonance imaging (MM), Ultrasound, and X-ray procedures, etc.) and diagnostic evaluation of the images produced from such imaging procedures that would be performed with an image evaluation (e.g., radiology read) by a qualified (e.g., licensed and credentialed) radiologist. It will be understood that the applicability of the presently described techniques and systems will extend to a wide variety of imaging data and other data representations produced by various medical procedures and specialties, including those not involving traditional radiology imaging modalities or radiology professionals. Such specialties include, but are not limited, to pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the AI model verification, execution, and workflow modification techniques described herein may apply to a variety of medical image data types, settings, and use cases, including captured static images and multi-image (e.g. video) representations.

Overview of Medical Imaging Environment

FIG. 1 provides an illustration of an example medical imaging system arrangement 100 (e.g., a radiology imaging arrangement), which enables the processing of data from medical imaging procedures with use of the examples described herein. The medical imaging system configuration 100 may be used for capturing medical image data in one location and for reviewing medical images associated with the data in another location. The medical imaging system configuration 100 may include many geographically separated imaging devices and many image review terminals, not shown. The medical imaging system configuration 100, in a radiology setting, may be embodied as a remote teleradiology system connected to a plurality of healthcare locations, as a localized radiology system used in a single hospital, healthcare provider network, or private radiology practice. The medical imaging system configuration 100 may also operate as an information processing network used to process data from respective imaging procedures regardless of the location of an eventual imaging evaluation.

For purposes of illustration, the medical imaging system configuration 100 depicted in FIG. 1 includes an image capture system 104, a workflow processing system 102, an image evaluation system 106, and a data processing system 108. The imaging system 104, for example, may include an imaging device 120, such as a CT scanner, a MRI scanner, or another imaging system (e.g., a radiology imaging modality). Using an energy source such as x-rays or magnetic fields, for example, the imaging device 120 may capture image data associated with a subject 122 (e.g., a patient). It will be understood that many other networks, systems, devices, entities, and actors are not depicted but may be involved in the medical imaging system configuration 100 and aspects of imaging, processing, workflow, or evaluation operations.

In an example, the imaging device 120 is controlled by a technician 126 at the medical facility through the use of a workstation terminal or other electronic input control 124. Prior to the technician 126 conducting the imaging procedure for a patient, information may be entered into or synchronized with the electronic input control 124. Information from an electronic medical record (EMR) or healthcare information system (HIS) may also be accessed or updated for the imaging procedure. Relevant information and metadata for the imaging procedure may be placed within the image data itself, or hosted within another data store for further access and processing. For example, the imaging device 120 may produce radiological images generally consistent with the Digital Imaging and Communications in Medicine (DICOM) format, other industry-accepted standards, or proprietary standards.

Consistent with the appropriate image format, the images produced by the image data source may include or be linked to metadata. This metadata may be generated by the imaging device 120, from input collected by the electronic input control 124, or from input from a HIS or EMR. Further, a series of images produced by the image data source may be obtained directly by the imaging device 120 in the facility shown in FIG. 1, or may be transferred in whole or in part from another image capturing device connected to the imaging device 120 or the medical facility's local network. The imaging data source may also include data transmitted through use of a local (e.g., on-premises) imaging server (not shown), such as a DICOM server or other Picture Archiving and Communication System (PACS). The metadata within each imaging data file may include identification information such as a patient identifier and an identifier of the series of images, in addition to information about the type of imaging modality and the techniques used to obtain the images. Further, for images formatted according to the DICOM standard, data fields such as a unique image identifier, a unique study identifier, the patient's name, and the facility from which the image originates may be included.

The image data generated by the imaging device 120 may include a series of two-dimensional images, with the collection of some identifiable series of images typically referred to as a "study." In some implementations, the image data may be used to produce a three-dimensional model that can be further manipulated and reformatted for generating two-dimensional (or three-dimensional) images. In other implementations, the image data may include three-dimensional models, visualizations, or graphical data generated by the imaging device 120 or intermediate processing systems. Image data captured by the imaging device 120 may be stored and processed by the workflow processing system 102 or another local or remote imaging device server (e.g., one or more computers with a processor and a memory), and may be provided to other systems and computers in the medical imaging system configuration 100 through network 130 (e.g., an intranet or the Internet).

In various examples, medical imaging procedure data provided to the workflow processing system 102 results in data being stored, processed, and communicated among one or more computers. For example, the workflow processing system 102 may determine that the medical imaging procedure data is to be forwarded to a particular computer associated with an evaluating user 142 (e.g., a radiologist workstation) at an image evaluation system 106. As shown, image data may be provided or directed by the workflow processing system 102 through the network 130 to the image evaluation system 106. Additionally, the medical imaging procedure data provided to the workflow processing system 102 results in the image data or related medical data being processed by the data processing system 108. This medical imaging procedure data may be processed by the data processing system 108 prior to, in parallel with, or at the same time as the provision or assignment of the image data to the image evaluation system 106. The data processing system 108 may assist actions taken at the image capture system 102, the workflow processing system 102, or the image evaluation system 106, through the use of AI and advanced data analytics. The data processing system 108 may utilize AI models and algorithms, among other rules or processes, to perform various aspects of data validation, recognition, classification, inferences, regression, prediction, or analysis.

The image evaluation system 106, for example, may include an image display system 144 (e.g., one or more computers with a processor and a memory), a display device 146 (e.g., a monitor), and input devices 148A-148B (e.g., keyboards, computer mice, joysticks, touch interfaces, voice recognition interfaces, and the like). In some implementations, image data may be processed by the image display system 144 and visually presented to the evaluating user 142 as one or more images or visualizations at the display device 146. Using the input devices 148A-148B, the evaluating user 142 may interact with the presented images or visualizations, for example, by manipulating one or more user controls included in a graphical user interface presented at the display device 146 in association with the images or visualizations. For example, the evaluating user 142 may view an image, a series of related images, or one or more visualization generated from an image, and may specify one or more adjustments, such as zooming, panning, rotating, changing contrast, changing color, changing view angle, changing view depth, changing rendering or reconstruction technique, and the like. By viewing and interacting with presented image data and with the user interface, for example, the evaluating user 142 may indicate, select, confirm, or input a diagnostic finding value related to a radiological imaging procedure performed on the subject 122. The image evaluation system 106 also may utilize a processing algorithm 145, including from AI models distributed or managed by the data processing system 108, to perform processing on the received study or other model input data 147.

The data processing system 108 may include a data processing server 152 (e.g., one or more computers with a processor and a memory). In some implementations, medical imaging procedure data (or images or individual data representations from such data) may be processed by a compiled binary or other software executed with the processor and the memory of the data processing server 152, to perform specialized image processing operations, among other operations. The binary or other software executed with the data processing server 152 may implement one or more AI models (provided by an artificial neural network, convolutional neural network, recurrent neural network, reinforcement learning model, natural language processing model, machine learning algorithm, decision tree, support vector machine, genetic algorithm, etc.) on the medical imaging procedure data, based on the use of model input data 154 and a trained processing algorithm 156.

In some implementations, AI data indications are produced by the data processing server 152 of the data processing system 108 to effect processing and changes for the subsequent workflows and evaluation activities of the medical imaging procedure data. In various implementations, the data processing server 152 may establish descriptors, markings, annotations, or additional metadata for images of the medical imaging procedure data; in other examples, the data processing server 152 may indicate the presence of particular identified conditions, the absence of certain identified conditions, the likelihood/probability/or other certainty score of such identified conditions, and other related outputs from the operation of a recognition algorithm on the medical imaging procedure data. Additional detail on the types of uses of AI models and AI-derived data processing is provided below.

When the workflow processing system 102 receives the image (or the image and the AI data indications), the system 102 may process the image with an image server for further handling in the evaluation workflow. This processing may include compressing or converting the image to a different format using a compressor/converter component. This image server may also operate to extract metadata from each image file in a series of images. For example, the extracted metadata may include header data for the image providing patient information and medical facility (e.g., hospital) information for the facility that sent the image. The image server may then store all or part of the extracted information in a study record that may be correlated with appropriate orders and studies. The workflow processing system 102 may operate to process related orders or correlate a particular order (and order data) with a particular set of study images (and image data). In some examples, the workflow processing system 102 operates to perform a lateral and horizontal movement of studies between an onsite facility and a remote/cloud location with a closely orchestrated feed utilizing HL7 (Health Level 7) and DICOM standards.

As discussed herein, the operations occurring at the workflow processing system 102, the image evaluation system 106, and other involved computing systems, may be affected by the outputs from the AI models that operate one or more algorithms on the medical imaging procedure data. Such outputs may determine or change the assignment of a particular study to a particular image review system, or the prioritization of a particular study in a worklist within a particular image review system. For example, the evaluation priority of a study within a worklist at an image evaluation system 106, or the assignment to one or more evaluation systems or radiologists, may be changed to a high status based on a time-sensitive identified medical condition such as an intracranial hemorrhage, pulmonary embolism, and the like. Likewise, the workflow processing system 102 may perform additional or substitute study assignments, verifications, data transfers, or other processing with the image evaluation system 106 based on a particular medical condition identified by the AI model, or metadata associated with the AI model processing (e.g., confidence level).

The data processing system 108 may serve as an orchestrator that selects particular AI models or processing approaches for use and execution, distributes AI processing tasks or models among local and remote settings, ensures accuracy and maintenance of the AI models, and the like. As discussed further below, execution of the AI model is not limited to operations at a single location of the data processing system 108; rather, multiple on-premises servers, edge computing servers, cloud computing servers, and the like (not shown) may be coordinated for model operations. Additionally, instances of the AI models (such as algorithm 145) may be executed at the image evaluation system 106 including on client computing devices during, before, or after the image evaluation process.

As one example, AI model processing may be invoked for the automated detection, classification, indication, or confirmation of certain medical conditions within the images, such as the detection of urgent or life-critical medical conditions, clinically serious abnormalities, and other key findings. The evaluation workflow activities which may be modified in connection with the techniques described herein, may include activities for a study having images that indicate a critical, urgent, or time-sensitive medical condition, such as: prioritizing the study in an electronic worklist of an evaluating user; re-assigning the study to a specialist who is proficient in diagnosing the critical medical condition; alerting a transmitting medical facility, an operations center, or one or multiple medical evaluators regarding the criticality of the study; identifying or labeling specific image locations in the study output based on the conditions identified in the study; and rearranging or reorganizing display characteristics of images or reporting data for the study based on the conditions identified in the study.

The AI models and algorithms discussed herein may be provided on behalf of any number of types of algorithms and trained models, including but not limited to machine learning models, deep neural networks, and trained feature detection algorithms that have been trained to perform image recognition, classification, data analysis, inferencing, or regression tasks, particularly involving data indicating certain types of medical conditions (e.g., medical images of human anatomy and anatomical representations). However, it will be apparent that the role of the AI models algorithms that are applied, used, and configured in the presently described medical imaging workflow and analysis activities may be supplemented or substituted by any number of other algorithm-based approaches, including variations of artificial neural networks, learning-capable algorithms, trainable object classifications, and other artificial intelligence processing techniques.

Figure 2:
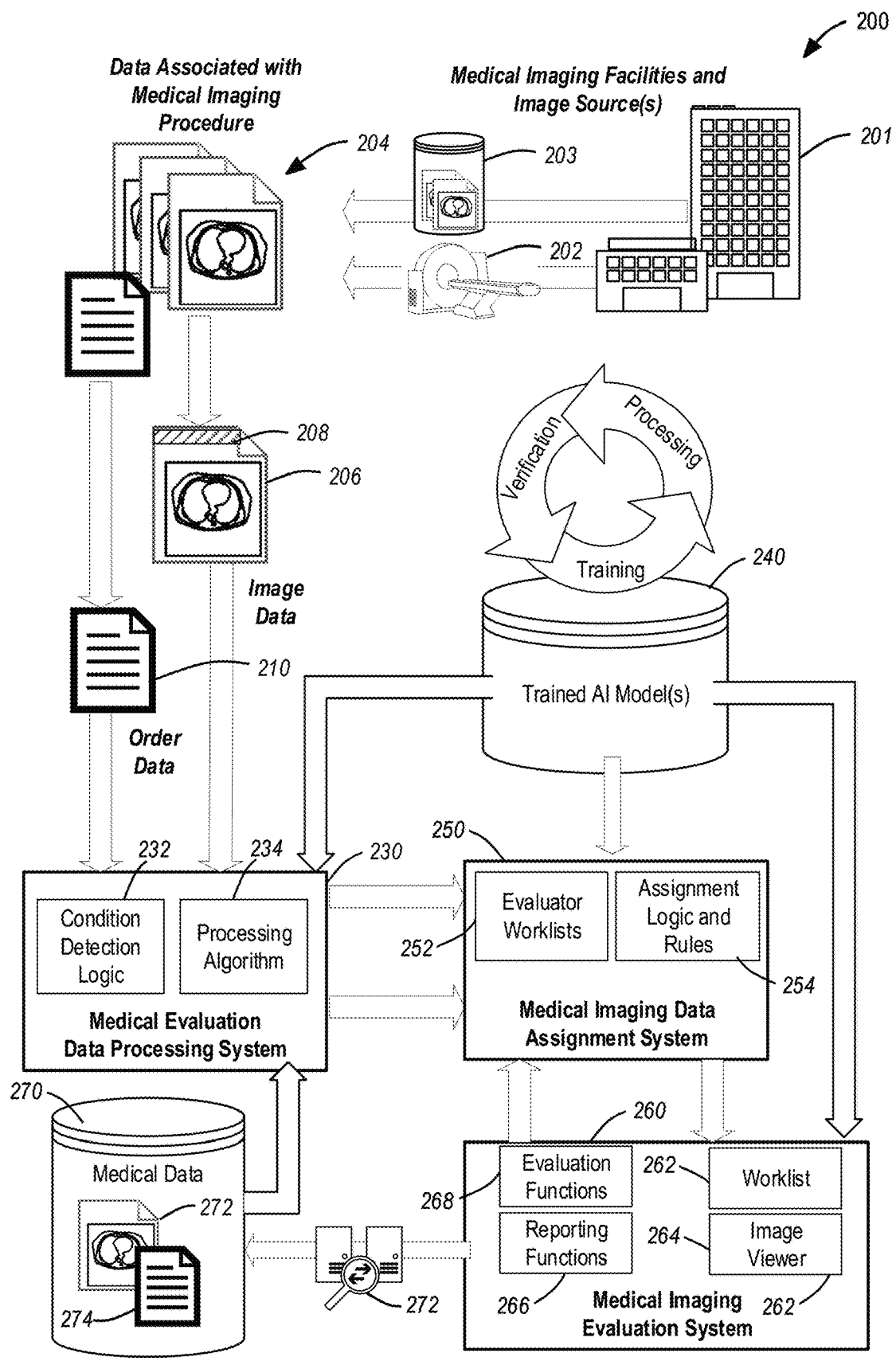
FIG. 2 illustrates system operations in a workflow for AI-enhanced analysis of medical imaging data produced from a medical imaging procedure, according to an example.

FIG. 2 illustrates a system operations diagram 200 of an example workflow for generating and communicating a set of data produced from a particular medical imaging study (e.g., a radiology study) with use of trained AI models 240 according to various examples. The trained AI models 240 assist data processing operations at a variety of computing systems, including with operations at a medical evaluation data processing system 230, a medical imaging data assignment system 250, and a medical imaging evaluation system 260. For instance, one or more AI models may be used to detect and triage certain medical conditions at the data processing system 230, based on image data indicated in the images or indicated from historical medical data; one or more AI models may be used to correct information and ensure assignment to a correct evaluator at the data assignment system 250; one or more AI models may assist image presentation or visualization, automate reporting, validate user input, or track evaluation actions at the evaluation system 260.

In detail, the system operations diagram 200 is depicted as including image data 206 and order data 210 originating from data of a medical imaging procedure (produced from an imaging modality 202 or obtained from a data store 203 at one or more medical imaging facilities 201), with the combination of image data and order data collectively referred to as imaging procedure data 204. It will be understood, however, that the imaging procedure data 204 may also be accompanied, integrated, or associated with information from medical information systems (e.g., EMR data, HIS data, and the like) that is not necessarily produced from the medical imaging procedure. Data from previous studies, evaluations, reports, and the like may also be considered or inferred.

The system operations diagram 200 illustrates a series of operations executable with an image processing system, such as the medical imaging system configuration 100 or specific components of the workflow processing system 102 and the data processing system 108. These operations include the receipt and processing of the imaging procedure data 204 (e.g., radiology study data, including one or both of a radiology order and a radiology imaging data) originating from a particular medical imaging facility or imaging source of the medical imaging facilities 201. This imaging procedure data 204 is processed to obtain identifying data associated with the medical imaging procedure, including an identification of imaging characteristics, type of the imaging procedure, and associated information related to the evaluation of the imaging data. For example, the medical imaging procedure data may include image data 206 and image metadata 208, where the image metadata 208 may include identification information such as a patient or study identifier and an identifier of the series of images, in addition to information about the type of imaging modality and the techniques used to obtain the images. The imaging procedure data 204 also may include order data 210 for an associated order to perform the diagnostic evaluation of the image data. For example, the order data 210 may be associated with data from an HL7 Order Message (ORM) sent when a healthcare provider requests a service, procedure, or treatment for a patient.

The imaging procedure data 204 may be provided to or assigned within the data processing system 230 for AI-coordinated processing of the image data 206 and the order data 210. For example, the data processing system 230 may implement automated image recognition through a trained image recognition model (e.g., provided by one or more AI models 240) with use of a processing algorithm 234 and other condition detection logic 232. Additionally, the condition detection logic 232 may select certain processing algorithms or image recognition models based on the characteristics of the medical imaging procedure indicated by order data 210 or image metadata 208. As one example, an image recognition model relevant to analysis of a medical condition within a human heart may be only applied to certain types of images captured from a patient's abdomen as indicated by the image metadata 208, whereas such an image recognition models would not be applied to images captured from outside a patient's abdomen. As another example, the condition detection logic 232 may perform a review of certain conditions based on the type of preliminary medical inquiries, known conditions, or findings indicated within the information of the order data 210.

In some examples, distinct processing algorithms and trained image recognition processing may be used to detect the characteristics of respective medical conditions; in other examples, a common model or series of algorithms may be used to detect or measure the likelihood of one or multiple of many identifiable medical conditions. In some scenarios, additional medical data 270 (e.g., data separate from the particular medical imaging procedure), such as information from a patient's medical history or records, previous imaging evaluations (such as prior images in medical image data 272 and reports in patient data 274), may be evaluated by the data processing system 230 to further improve the accuracy and operation of the processing algorithm 234.

The data processing system 230 may be used to generate an indication of one or more medical conditions or image states detected from image data, and generate associated details and launch processing activities for such medical conditions. The details for such medical conditions or image states may include a confidence level for the presence or absence of certain conditions (e.g., a score that corresponds to a level of recognition of whether certain conditions are or are not detected), identification of specific features or areas in the image in which certain conditions are detected or likely to occur, identification of images in the study in which certain conditions are detected or likely to occur, and similar identifications and indications.

The one or more trained AI models 240, for example, may be embodied by a computer-generated deep convolutional neural network trained by numerous historical studies and expert results, including with the use of supervised learning (e.g., training from a labeled data set) or unsupervised data (e.g., training from an unlabeled data set). These studies and results may include the same format and content as the medical imaging study to be evaluated, or may take a derivative or alternate form. The training of the AI models 240 thus may be provided as a result of earlier evaluation actions at the evaluation system 260, or other human created or verified results from prior workflow or training activities. With use of the trained AI models 240, the data processing system 230 is able to produce accurate and detailed results of machine detected objects and conditions through a data-driven cycle of training, processing, and automated verification of results. Such verification may be in the form of automated or manual feedback used for training or re-training models, generating accuracy or compliance statistics, or other remedial or informative actions.

Results data from the evaluation of images of the particular study with an AI model may be provided to a data assignment system 250, with such model outputs used for purposes of affecting an assignment or evaluation of the study at one or more selected evaluators, correction or validation of data associated with the study, or the like. For example, the study and its associated data may be assigned to one or more selected evaluators for diagnostic interpretation, analysis, or other human evaluation of the image data 206. The model outputs from the data processing system 230 may be used to modify evaluation activities or graphical outputs, obtain new data or new inputs, or the like.

The data assignment system 250 may also maintain a series of evaluator worklists 252 that are used to propagate the assignment of studies to respective evaluators, with the evaluator worklists 252 and accompanying graphical user interface outputs being affected (e.g., reordered and adjusted) by the model outputs. The data assignment system 250 also may use a set of assignment logic and rules 254 to determine the appropriate assignment of studies to the respective evaluators, which may be affected by the model outputs from the data processing system 230. For example, a serious and time-sensitive medical condition identified by an AI model may result in the study (and its associated data operations and processes) being escalated, prioritized, or alerted within multiple of the evaluator worklists 252, to reduce the amount of time it takes for at least one evaluator to begin evaluation of the study in a timely manner.

Also, the data assignment system 250 can operate to provide imaging data to an evaluation system 260 operated by a respective evaluator. The evaluation system 260 may include a worklist 262 of assigned studies to review by a particular evaluating user; an image viewer 264 to output and control the display of various images from the image data; reporting functions 266 to collect and compile a diagnostic report for medical findings from the image data; and evaluation functions 268 to assist the user with automated or AI-driven actions on the image or report data. The results data provided from the data processing system 230 or from other instances of AI models may be used to modify the order, orientation, hanging, or positioning of particular images, series, or comparison studies (for example, to quickly indicate, highlight, or display images including significant medical findings). These modifications may be implemented in a display or graphical user interface automatically, or in response to user selection (e.g., in response to alerts and user-selectable options in a graphical user interface that can quickly implement modifications and suggested actions).

Although not expressly depicted within FIG. 2, other data flows may be established or updated between the data processing system 230 and other components of the data assignment system 250 and evaluation system 260. These data flows may propagate information relating to image annotations, preliminary image findings and report data, order data modifications, and the like, and data values for these fields of information may be implemented in connection with the image viewer 264 or other aspects of the assignment logic and rules 254 or the reporting functions 266. Additionally, the operations performed in connection within FIG. 2 may be implemented with features of a PACS or RIS, features of a HIS or data informatics system, or other components of a medical image procedure management system. In other examples, the data from the machine learning system may be communicated or propagated throughout the system in the system operations diagram 200 to facilities and other users as part of display preferences, report data, or other relevant data indications.

The prioritization of a study in the evaluator worklists 252 is merely one example of operations that may occur in a workflow which is driven by the detection of a medical condition or some other scenario. Other examples of modifications to the workflow may include: implementation of a protocol that operates to unbundle and distribute images from multiple anatomical locations to multiple evaluators; prioritization and other processing activities to certain specialists within a specialized (e.g., stroke or cardiac condition) workflow or like workflows tailored for time-sensitive or specialized medical conditions; identification of specific imaging features or data values through annotations, highlights, flags or alerts; identification or correction of incorrect information in metadata; extraction or identification of prior medical information or report information; execution of additional or different AI models; modification of AI model execution behavior; and the like.

AI Model Execution Management

The following AI model execution management techniques address the need to orchestrate data and traffic, and to match AI models, input data, and execution actions at an appropriate location. In particular, in a time-sensitive setting or with limited computing resources, there may be data items that should (or should not) be processed with specific AI models. Due to the large number of AI models that have become available, and the expansion of the amount of possible input data relating to a human subject, it is simply not practical to run every possible model or algorithm on every possible piece of data. Even if computing resources were available to securely analyze all possible models and all possible data, the results would not be produced in a timely manner or might be inconsistent with each other.

Prior approaches for AI processing often relied on cloud-based processing to manage AI-enhanced workflows. Such approaches often placed a limited number of AI models at a single execution location in the cloud, requiring uploads of all imaging data to the cloud; then, high powered computing equipment could run selected AI models, and a client would then obtain or download all results from the AI model processing. This prior approach presents a number of problems related to security, privacy, and overall risk; this prior approach also presents issues of scale as the amount of medical procedure data and number of applicable AI models continues to grow.

The following AI model execution management approach involves the concept of an inference engine, coordinated among one or multiple execution locations. One or more inference engines are orchestrated to identify which AI model should be run on input data, and to execute the model either at a local location or a remote location. The identification of an AI model may determine whether the model is applicable to the data being evaluated, and that the model is licensed and can be run at that location. Different types or layers of AI models can be executed to identify different characteristics, features, or properties of the input data; depending on the state of the input data, the type of input data, or other characteristics, a wide variation in execution can be accomplished.

Figure 3:
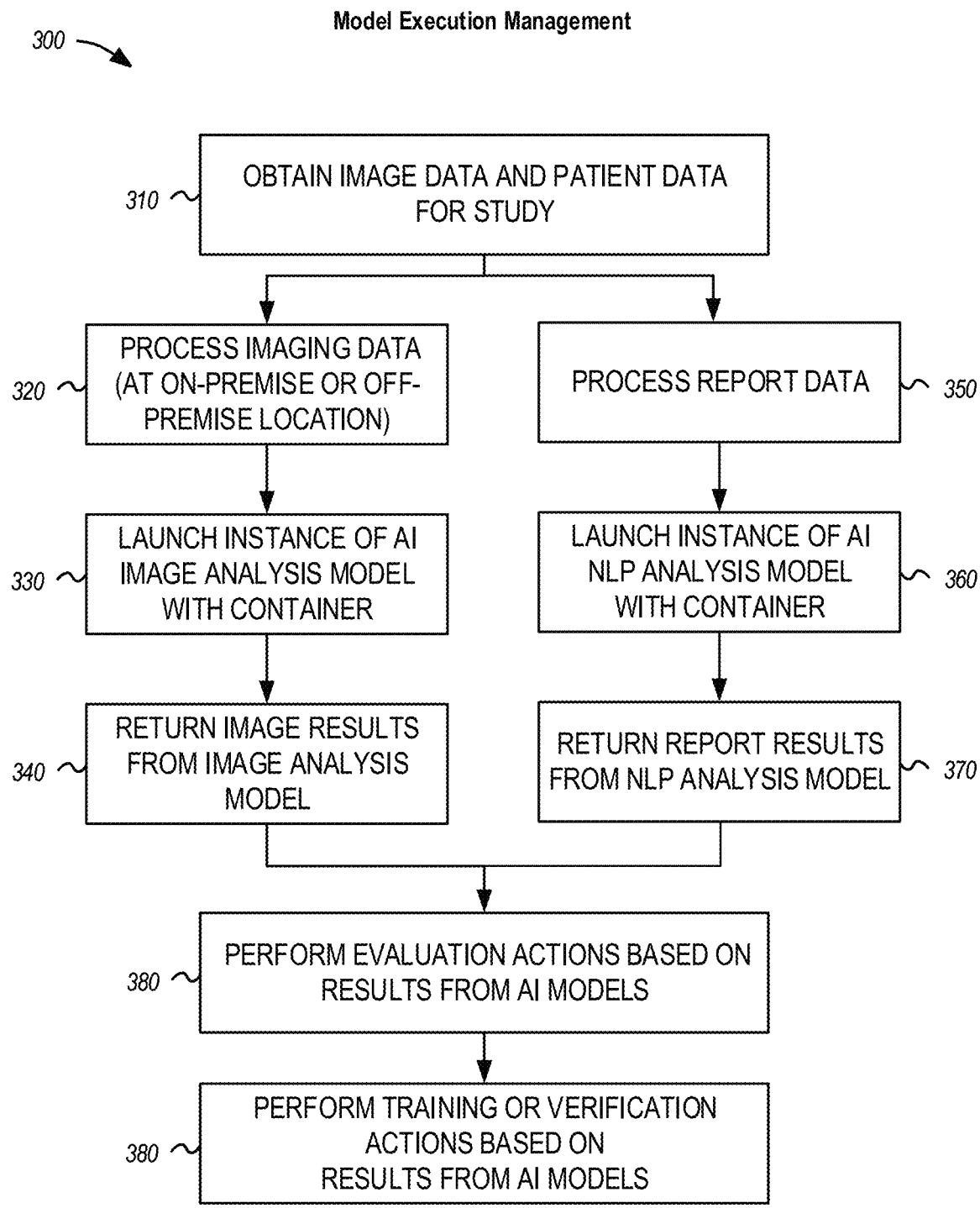
FIG. 3 illustrates a flowchart of operations performed in an AI model execution management process, used for processing of medical imaging data, according to an example.

FIG. 3 illustrates flowchart 300 of operations performed in an AI model execution management process, used for processing of medical imaging data. As shown, the example flowchart 300 may be used for implementing the condition detection, assignment, or evaluation features discussed in FIGS. 1 and 2, or the use cases further discussed below.

In operation 310, image data and patient data (e.g., order data, image metadata, health records data) are obtained for a particular study evaluation. Based on the type of data, type of study, available processing resources, or other characteristics, processing of the data is orchestrated and coordinated among on-premise and off-premise (e.g., cloud) locations. This is shown in more detail in FIGS. 4 to 7.

In operation 320, the imaging data is identified to be processed at on-premise or off-premise locations. This may occur, in operation 330, by launching an individual instance of an AI image analysis model with a container at the execution location (if not already running). In operation 340, the image processing results are returned from the AI model. As suggested herein, these image processing results may be in the form of inferences, classifications, values, identified image objects or areas, and the like.

Processing is performed in operations 350-380 to provide additional analysis of relevant data characteristics, based on natural language processing. For instance, prior radiology reports from the patient may be analyzed to determine which AI model(s) to execute, whether additional data of the patient should be retrieved or accessed, whether to perform additional analysis on imaging data, and the like. This processing may be performed in parallel, or before or after the imaging data analysis of operations 320-340.

In operation 350, report data is obtained and processed (e.g., extracted, identified) from reports associated with the subject or study. In operation 360, one or more instances of NLP analysis may be performed on the reports, such as launching an AI model with a container and providing the report text as input to the model. In operation 370, results are returned from the AI model; these text processing results may be in the form of inferences, classifications, values, labels, identified characteristics, and the like.

In operation 380, evaluation actions are performed in an image evaluation workflow based on results from the image and language processing AI models. These evaluation actions may include the use cases discussed further below. In operation 390, additional training or verification actions (or, remedial actions) may be performed during or after the evaluation workflow based on the results from the image and language processing AI models.

In an example, the model execution can be managed through use of an inference engine architecture which provides an orchestration layer between the platform and the execution of the model. An inference engine takes the right study and the right model and puts them together, and directs the results of the model processing. An inference engine can launch a container with an AI model or algorithm at the location of the data, instead of needing to send the data to a cloud service where the AI model exists. The results from the AI models executed by the inference engine then can be coordinated and communicated back to a PACS or RIS system, to an evaluator system, or to other data processing or storage locations.

An orchestrated inference engine architecture provides a number of technical benefits. For instance, the architecture can scale with the workload, manage multiple versions of the same model, decide where to run the model (on premise/locally or in the cloud), use more GPUs or specialized hardware at different locations, and the like. Decisions for AI execution can be based on resource allocation, the type or characteristics of data to be processed, timeliness, or other considerations.

The use of an orchestrated inference engine architecture also enables the addition or removal of AI models and algorithms, without affecting the underlying platform. In addition to the scalability benefits, this architecture can integrate with many aspects of model measurement, governance, and verification, as discussed in the examples further below.

Figure 4:
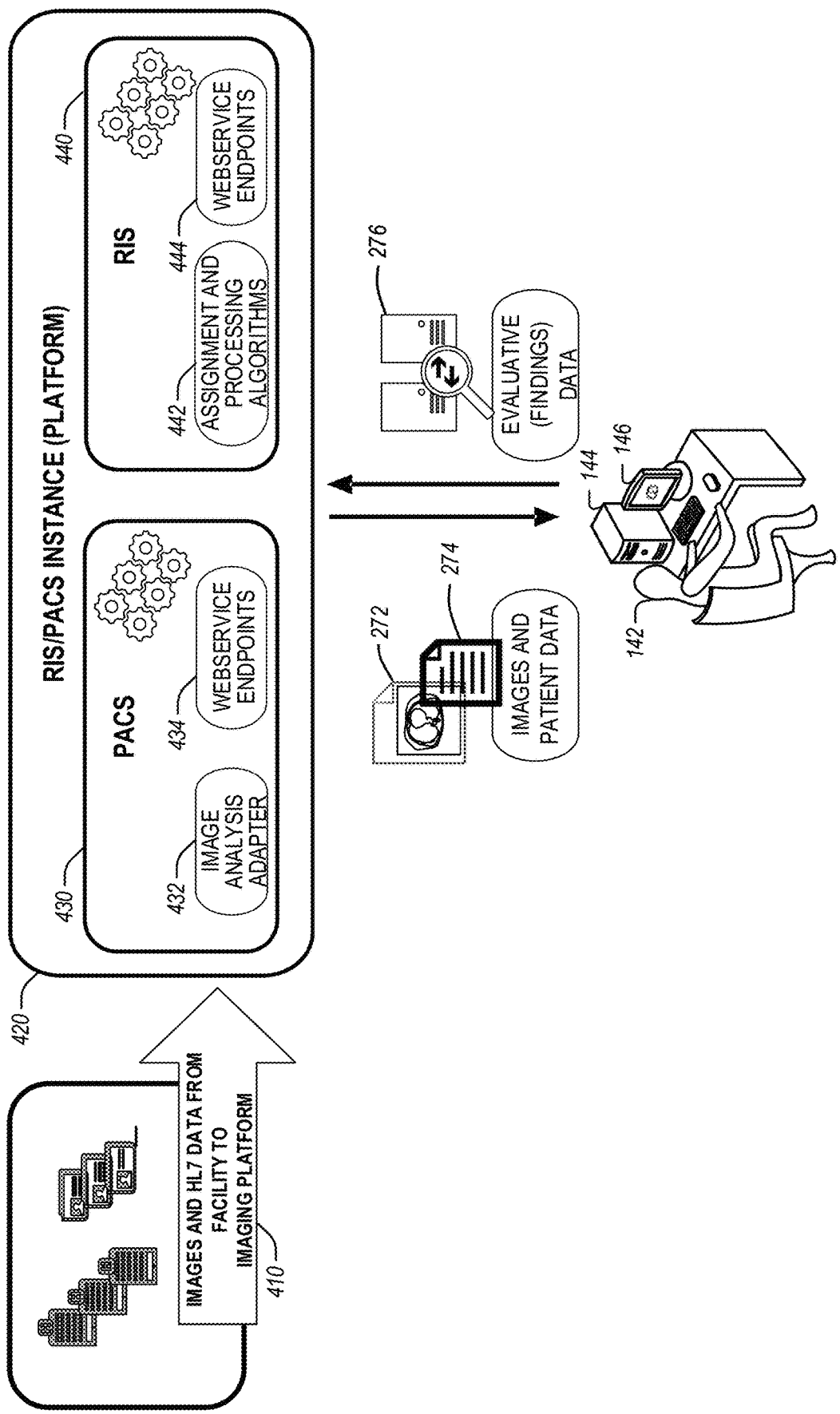
FIG. 4 illustrates a diagram of medical imaging processing with a radiology imaging platform, according to an example.

FIG. 4 illustrates a diagram of medical imaging processing with a radiology imaging platform, such as in an RIS/PACS instance operating on a medical imaging data processing platform 420. The platform 420 is depicted as including a PACS 430, which provides Picture Archive and Communication System (PACS) functionality, a viewer, and other components not shown; and a RIS 440, which provides a Radiology Information System (RIS) functionality for managing the radiology workflows, including order creation, worklist applications for the operations center and radiologists, and case pages for the radiologist.

The RIS 440 includes web service endpoints 444 that are used for communication with the RIS from other entities (including with an Inference Engine, discussed further below). The RIS system also includes assignment and processing algorithms 442 to manage the worklists, orders, and perform other data processing.

The PACS 430 also includes webservice endpoints 434 that are used for communication with the PACS from other entities (including with an inference engine, discussed further below). The PACS 430 also includes an image analysis adapter 432 to invoke one or more AI models (including via the inference engine) when new image data and metadata are obtained. It will be understood, that these or other functionalities may be performed by other engines or subsystems, and other aspects of the RIS 440 and PACS 430 are not depicted for simplicity.

In a basic example, the platform 420 is configured to communicate with a workstation (e.g., an image display system operated by an evaluating user 142) to provide data and assist the display of data on the display device 146. In its simplest form, image data 272 and patient data 274 are communicated from the platform 420 to the workstation, where the evaluating user enters or confirms evaluative data 276 (such as radiology findings) including functionality that is identified, enhanced, or modified with the use of AI models.

Figure 5:
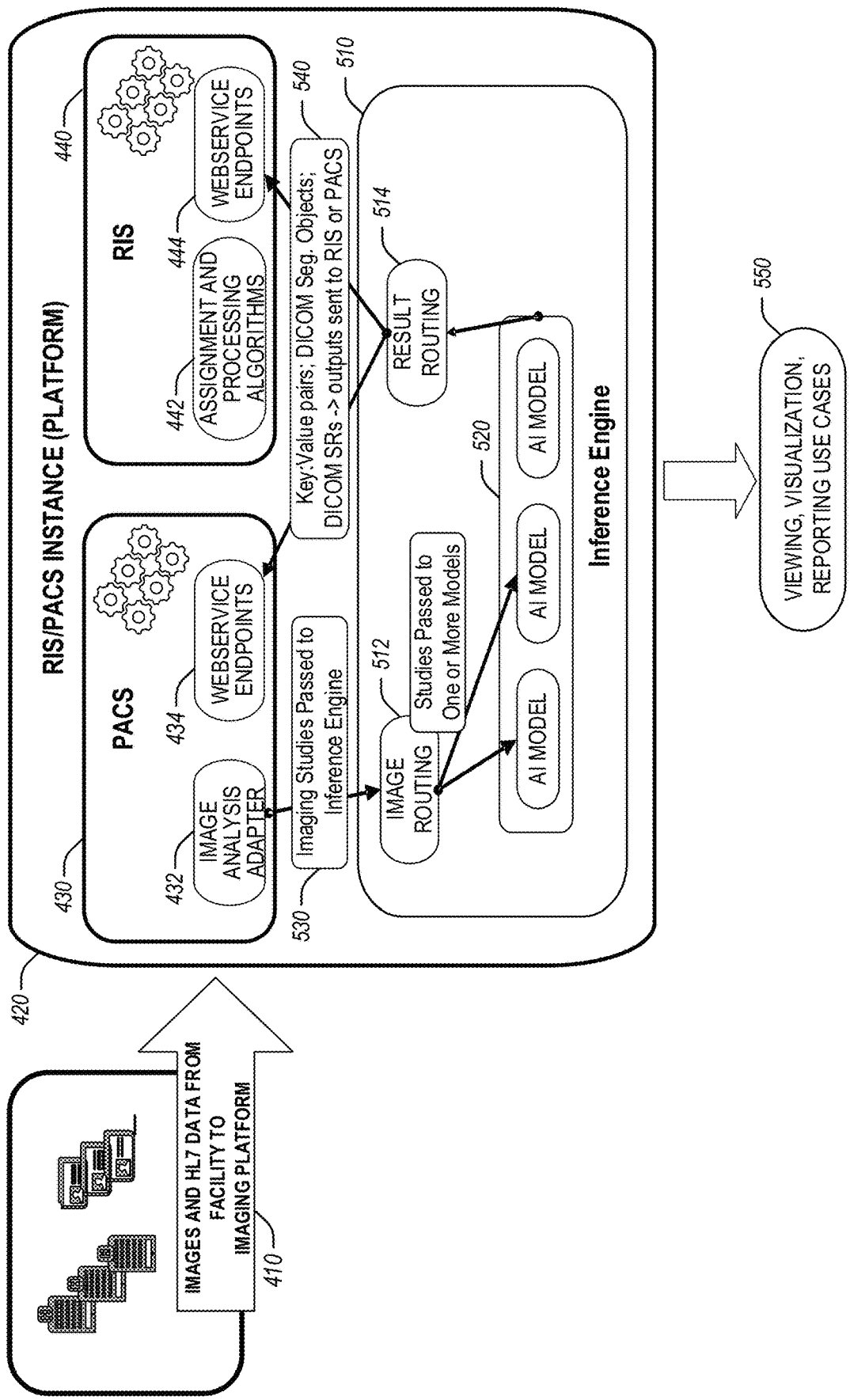
FIG. 5 illustrates a diagram of medical imaging processing with an inference engine in a radiology imaging platform, according to an example.

FIG. 5 illustrates a diagram of medical imaging processing with an inference engine 510 operating in the medical imaging data processing platform 420. Similar to the approaches discussed above, the processing within the platform 420 may be used for variety of viewing, visualization, and reporting use cases 550, such as with radiology reads, discussed throughout this document. Building on the architecture introduced with FIG. 4, use of the inference engine 510 further involves imaging studies data 530 being passed to the inference engine 510 from the PACS 430, and results being provided back to webservice endpoints 434, 444 of the PACS 430 and the RIS 440 from the inference engine, based on AI model data processing.

In an example, the inference engine 510 is sent messages from a PACS 430 or other medical imaging repository about images available for inferencing. If the inference engine 510 desire to run an inference on the given images using a particular AI model, the inference engine 510 will receive the images through image routing components 512. Then, the inference engine 510 will determine which AI models to use for the purposes of inferencing, through execution of one or more AI models 520 being deployed with one or more containers. After execution of the AI models 520 on the imaging studies data 530, results from the models are collected at a result router 514 where data is stored or forwarded on to other pieces of technology for further action. Finally, the inference engine 510 initiates one or more automated actions based on the data collection, including reporting and alerting based on data values 540 produced by the AI model (e.g., key:value pairs, DICOM segmentation objects, DICOM structured reports, or other model outputs) to the PACS 430 and RIS 440.

Figure 6:
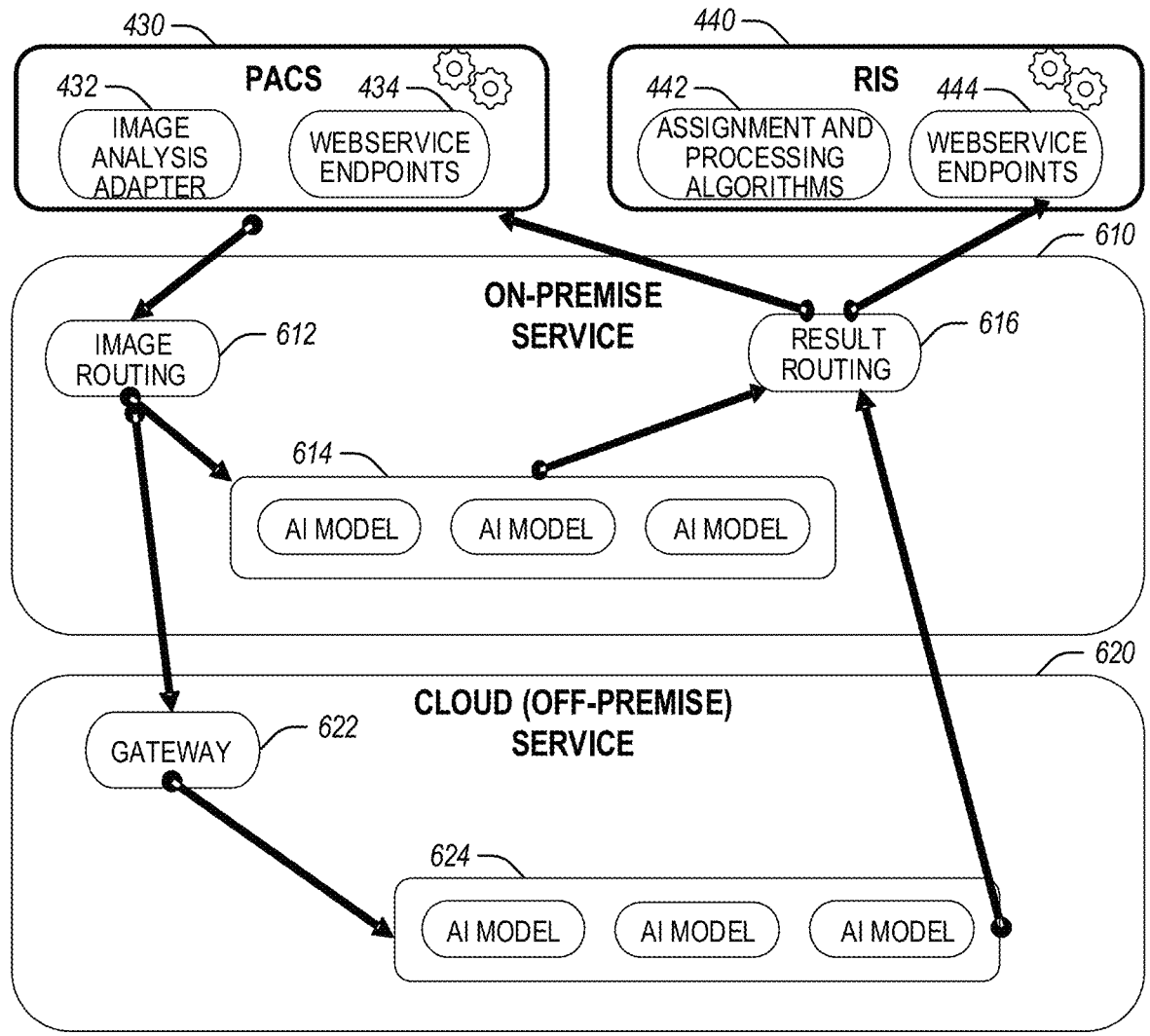
FIG. 6 illustrates a diagram of medical imaging processing among multiple services with a distributed radiology imaging platform, according to an example.

FIG. 6 illustrates a diagram of medical imaging processing among multiple services with a distributed radiology imaging platform. In this scenario, the PACS 430 and RIS 440 described in FIGS. 4 and 5 is extended to provide distributed execution of AI model operations of an inference engine at a local, on-premise service 610 and at a remote (cloud) off-premise service 620.

The initial operations of image router 612 and selected execution of one or more AI models 614 occurs at the on-premise service 610; however, additional processing occurs with selected execution of one or more AI models 624 at the off-premise service 620. The image router 612 at the on-premise service 610 may coordinate with a gateway 622 at the off-premise service 620, and all of the results from the AI model processing may be provided back to a report router 616 at the on-premise service. With the use of containers or other lightweight execution instances, the models 614, 624 may be easily started and orchestrated for execution at a particular location, and results returned to the appropriate PACS and RIS instance.

Figure 7:
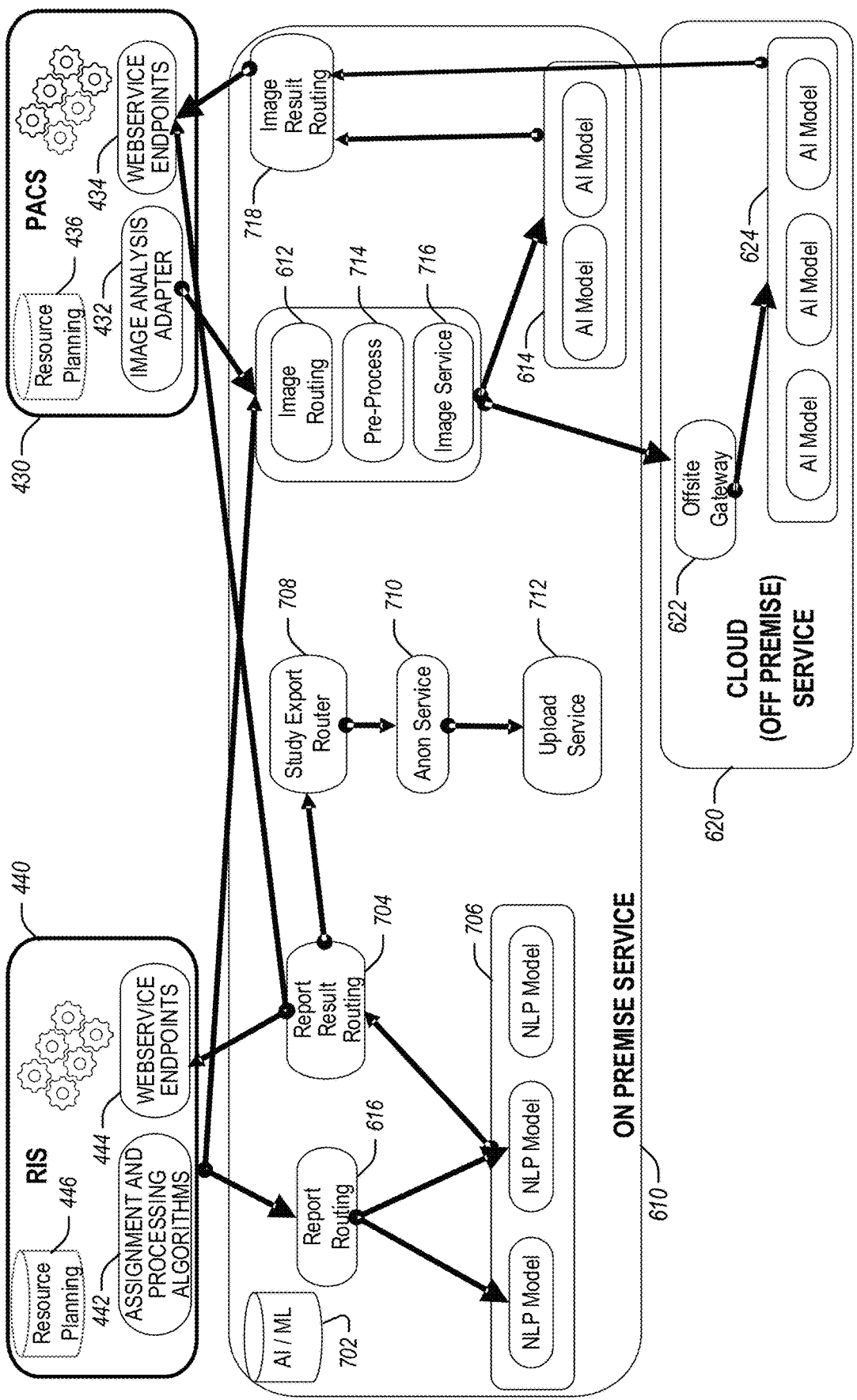
FIG. 7 illustrates a diagram of medical imaging processing among multiple services with AI models operated by an inference engine configuration, according to an example.

FIG. 7 illustrates a diagram of medical imaging processing among multiple services with distributed AI models operated by an inference engine configuration. Building on the architectures introduced in FIGS. 4, 5, and 6, the operation of the RIS 440 and PACS 430 are further coordinated for execution of specific operations at both on-premise and off-premise services 610, 620. In this example, the RIS first provides communications to an inference engine of the on-premise service 610 to generate a report inference, using communications between the RIS 440 and the report router 616. For instance, RIS components, such as RIS webservice endpoints 444, may send data to an inference engine at the on-premise service 610 based on data received at the report router 616.

The functional part of the inference engine operations (e.g., at on-premise service 610) may be operated on-premise to include image and result routing, as well as execution of select AI inference models themselves. The off-premise operations of the inference engine (e.g., at the cloud service 620) are coordinated with a gateway to reduce data transmissions over the network. For instance, if more than one off-premise model will receive the same image study, then the gateway 622 coordinates the image study at one time and disperses to the appropriate models. Off-premise processing can be used for a variety of model inferencing operations, as inferencing is scaled up and down for various needs (e.g., as detected from the characteristics of the data, or as orchestrated for other reasons).

The image analysis adapter 432 of the PACS 430 may send a message to the inference engine each time a new study is ingested by the PACS 430. The information sent may not be the full study (images), but some metadata used by the inference engine to determine if the study should be retrieved and sent to an image AI model. The RIS 440 can send data and message to the image router 612. This might be information entered by a radiologist technician through an order management system, information from HL7, or other data that can assist the inference engine. Additionally, the PACS 430 can provide communication between the image analysis adapter 432 and the image router 612.

In an example, image routing may be performed by components including an image router 612, a pre-processing service 714, and an image service 716. The image router 612 is responsible for receiving messages from the PACS 430 or MS 440, pulling studies from the PACS 430 (e.g., via the webservice endpoints 434), and sending studies to the appropriate image processing AI models 614. For some models, studies can be transformed by the pre-processing service 714 in various ways, including transforming data into multi-dimensional data sets (e.g., Numpy arrays) or other formats for easier ingestion by Image AI models.

The image service 716 can help add information valuable to routing, analysis, or evaluation by running specific models to ascertain additional information pertinent to routing prior to routing to further models. This might include body region analysis, X-ray View-Type information, and CT Contrast information, in addition to other metadata useful in determining which Image AI models should receive the study for analysis.

For use of On-Premise AI models, the Image Routing components may send data directly to the AI Models 614. The AI Models 614 may be launched with on-premise execution, such as by the execution of AI models that are containerized with Docker. For use of off-premise AI models, the image routing components may send a study as well as off-premise routing information to the off-premise gateway 622. The gateway 622 acts as a type of forwarding component such that if there are more than one image AI models off-premise that will be getting the same study, the study is only sent one time and the offsite gateway 622 is responsible for forwarding the study to multiple models. The offsite gateway 622 is responsible for receiving studies from the image routing components and passing each study to one or more models. A study is only transferred one time to the offsite gateway 622 which then can pass the same study to multiple models. This component thus reduces data sent off-site. The off-premise image AI models 624 also may be containerized with Docker.

The AI models 614, 624 return results to the image result router 718. The image result router 718 is responsible for receiving results from image AI models and sending those results to other systems, including the RIS 440 and PACS 430. For instance, the image result router 718 may send results to the PACS webservice endpoints 434 and the RIS webservice endpoints 444.

The report routing components operate within the service 610 to communicate data and metadata to appropriate locations. For instance, the report router 616 routes incoming reports to various report data analysis models, and includes queues and retry logic. In the depicted example, the report router 616 provides communication to NLP models 706 to provide report data for natural language processing. Based on operations of the NLP models 706, the results of from the NLP models are communicated to a report result router 704. In a specific example, the NLP models may be hosted in Docker containers and executed on demand, to run the AI inference for natural language processing and then pass the results on to the report result router 704.

The report result router 704 is responsible for receiving the results from these NLP models and passing them on to other systems, including PACS 430 and RIS 440. The report result router 704 sends NLP results to RIS webservices endpoints 444 to be used and/or stored in the RIS 440; the report result router 704 also sends NLP results to PACS webservices endpoints 434 to be used and/or stored in the PACS 430. The report result router 704 also sends information, such as positive reports, to the study export router 708. This communication may be integrated into the automated extraction of data for the purposes of training image AI models. The study export router 708 may be used for managing study exporting for the purposes of extracting anonymized data from the PACS 430 to provide to a staging location for the data to be used for training and/or validating of Image AI models.

The study export router 708 is used to queue studies for export by gathering them from the PACS 430 (e.g., through webservice endpoints 434), as well as retrieving reports and sending them to an anonymization service 710 to be anonymized. The anonymization service 710 is responsible for removing PHI from DICOM tags, removing personal health information (PHI) from reports, and other actions such as marking x-ray (XR) images with burnt in PHI as non-extractable. It will be understood that a variety of processes and techniques for anonymization may be implemented; and the techniques for anonymization may also be integrated with a validation protocol used to test anonymization.

Once a study and report are anonymized and checked for burnt in PHI, the data is sent to the upload service 712. The upload service 712 is used for uploading extracted and anonymized data to a staging area for usage in training and validating AI models (e.g., via a secure upload or secure FTP (SFTP) site). Some of the example uses of training and governance are discussed further below.

AI Workflow Execution Management

In an example, a variety of processing workflows may be initiated or changed through the use of AI processing techniques. This may include various aspects of verification and correction, such as to identify and correct certain detected conditions within imaging or order data; worklist prioritization, such as to prioritize, de-prioritize, re-assign, or modify status of a radiology read within a worklist; execution of additional AI models or backup models or algorithms, based on AI-detected conditions; or, verification or governance actions, based on AI-detected conditions.

AI models are commonly used for analyzing images, such as with convolutional neural networks, for identifying, classifying, and labeling characteristics. Such determined characteristics can be used to ensure data integrity in parts of the radiology workflow by automating the correction of mistakes or automating the input of data to avoid mistakes in the first place. Also within this category, AI models may be used to determine the presence of medical findings on images and then use those findings to take action on the corresponding study or present findings directly to radiologists.

As an example, a workflow enhancement may include worklist prioritization based on AI-detected or probable conditions for critical, acute positive pathologies such as intracranial hemorrhage (ICH), pulmonary embolism (PE), pneumothorax, aortic dissection, and pneumoperitoneum. In another example, the workflow enhancement includes the performance of image data verification or non-image data correction. For example, machine vision based error correction of incorrect data can be used to identify contrast even if it was not identified in the radiology order.

In another example, the workflow enhancement includes data correction. For example, pixel based images and order data, when decoupled from one another, may present a high error rate between what metadata indicates and the image indicates. This may be in the form of an ultrasound procedure that does not match its description; an incorrect number of images or type of scan; or a variety of other mis-entered or corrupt data. Such errant data may lead to a billing error downstream, or even missed or mis-diagnosed conditions.

A variety of other aspects of alerting, validation, correction, identification, and arrangement actions may be implemented by AI models to assist with the pre-processing, evaluation, and post-processing in image evaluation and processing workflows. For example, an AI model may evaluate a set of images to validate a procedure description, to ensure that anatomy is correct; that the contrast dose indicated in metadata is correct; and to ensure that correct subspecialty flows are implemented. This type of processing can help ensure data integrity between what was ordered and submitted. This may be automatically performed as part of a "DICOM Discrepancy Detector" that is used to identify a difference between information indicated in DICOM metadata and information reflected in images. This may also be automatically performed at other times or areas of an evaluation workflow.

Figure 8:
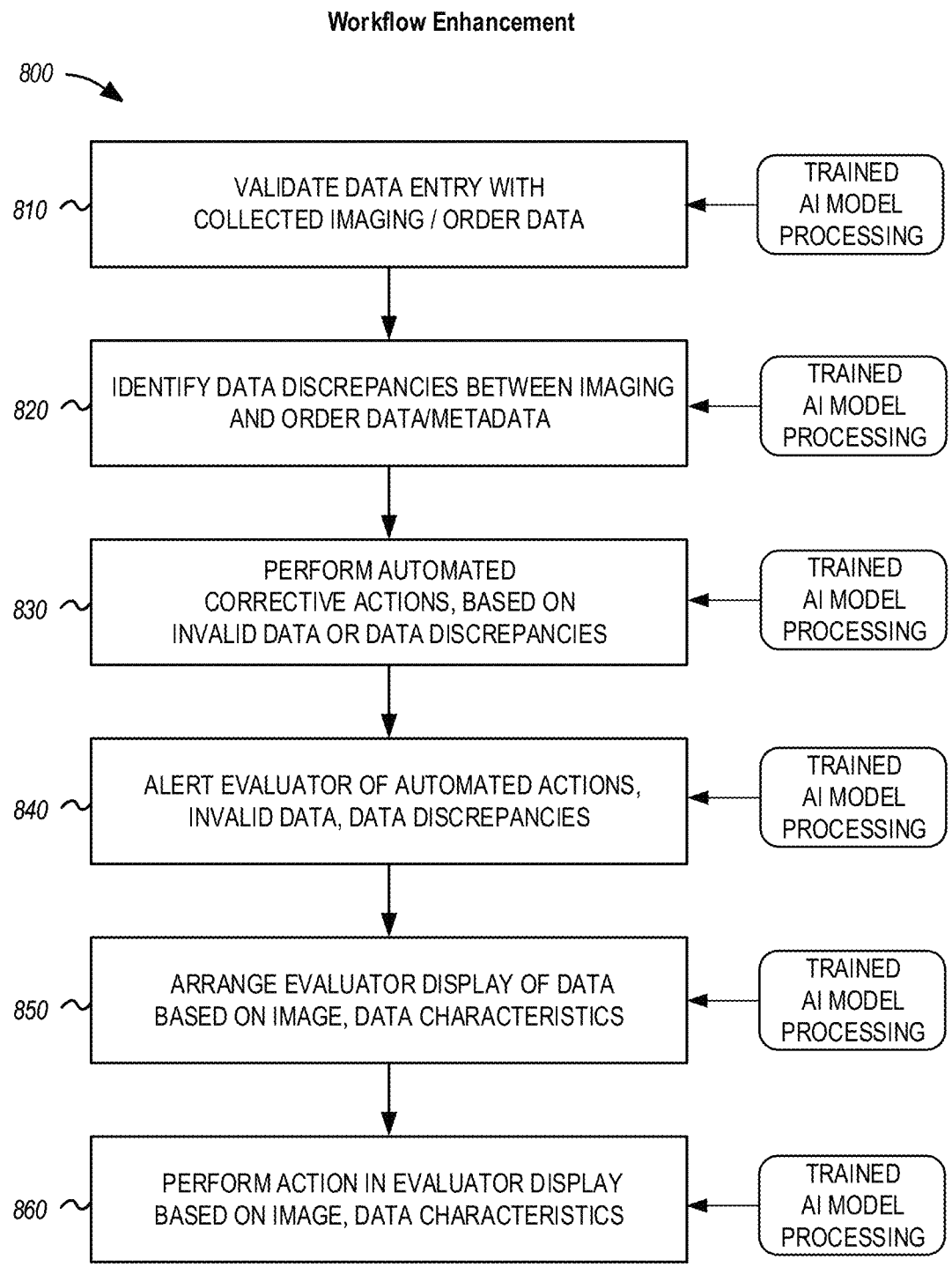
FIG. 8 illustrates a flowchart of example workflow operations performed for processing data of a medical imaging study, according to an example.

FIG. 8 illustrates a flowchart 800 of operations performed for processing data of a medical imaging study, as enhanced by AI model processing from one or more AI models. These operations may be performed in an image data processing system such as the systems depicted in FIGS. 1 and 2, or as coordinated within the RIS/PACS processing platforms and inference engine depicted in FIGS. 4 to 7.

The flowchart 800 specifically provides examples of operations that can be used to automatically identify, arrange, or correct data based on analysis of the images to improve the radiology workflow. This includes many variations in use cases, each of which may use the results from one or more trained AI models.

At operation 810, data entry may be validated using a trained AI model, based on the collected imaging or order data. Validating data entry may include scenarios when a radiology technician enters data such as the "exam" being performed, to ensure that the images that were sent match the exam being ordered. For example, if a technician sends an x-ray study with 3 unique views, but tries to choose an exam with only 2 views, the technician can be alerted to the discrepancy to avoid incorrect billing later in time. Another similar example is ordering an ultrasound of the pelvis only and the images contain slices and angles for a transvaginal non-OB study—the technician can be instructed to correct the data for correct processing.

At operation 820, data discrepancies between imaging and order data (or other medical metadata) may be identified, using a trained AI model. For instance, identifying data discrepancies may include identifying some errant characteristic of an order with the AI model, and then automatically alerting a technician regarding the error in the order before all images are sent from the medical facility. Similar to the above, a technician may already have chosen the exam and the order is in process when more images arrive. If the discrepancies are identified, the technician can be alerted to correct the mistake.

At operation 830, one or more automated corrective actions may be performed in an evaluation workflow, based on results from a trained AI model. These corrective actions may be identified based on invalid data or data discrepancies among the imaging data, order data, report data, etc. Such corrective actions may be automatically implemented for only some use cases, subjects, or clients; in other examples, suggested corrective actions may be provided through detection and alerting, with user control to accept or reject the suggested corrective actions.

At operation 840, one or more indications may be provided to an evaluator that indicate invalid data or data discrepancies. For instance, if a study is provided to a radiologist and the radiologist does not notice the discrepancy during their review of images, an alert can be provided to the radiologist. A variety of automated actions, suggestions, indications, and messages may be provided to seamlessly integrate with evaluator image review tasks.

At operation 850, actions may be taken within the evaluator display, based on the image or data characteristics detected by a trained AI model. For instance, with certain studies, the radiologist may want the images "hung" in a certain way. For example, while reading an X-ray Chest View, the radiologist may want the AP/PA view on the first monitor and the lateral view on the second monitor. The study may be automatically hung (e.g., with specific hanging protocols) based on characteristics determined and verified by the AI models.

At operation 860, further actions may be performed in an evaluator display based on image or data characteristics detected by a trained AI model. For instance, this may involve document detection (e.g., because many workflows require knowledge of whether an image is a scanned document), the implementation of hanging protocol, determining whether data is missing or in-process (e.g., whether all images have been received from a facility), or determining if a certain series should be automatically opened as a prior comparison.

As non-limiting examples, the following features or conditions may be detected from a trained AI model:
  i) Ultrasound: detect if the ultrasound study is a specific type of study that requires specialized evaluation (e.g., Transvaginal Non-OB).
  ii) Chest/Abdomen/Pelvis anatomical areas: Utilize an AI model that classifies CT images into body regions, to verify that the radiology order matches the provided images.
  iii) X-ray—Chest Views: Detect AP/PA vs. Lat images, and the number of views, prior to processing.
  iv) XR—Foot or Ankle Images: Identify the number of views.
  v) Contrast vs. Non-Contrast vs. Both: Determine whether the study images includes contrast, and whether the order data correctly or incorrectly notes this condition.

For any given detected pathology or condition, one or more of the following workflow steps may be implemented:
  i) Gather data for automated analysis of an AI model for a condition/pathology to validate that the model works at large scale.
  ii) Prioritize a study on the RIS worklist for reading sooner.
  iii) Place a study with a likely "miss" (the AI model detected a finding, but the evaluating radiologist missed the finding) into a pool of 'overreads' that one or more other radiologists are required to review.
  iv) Place a study automatically into a discrepancy detected workflow that performs a QA process on radiologist findings (e.g., provided with automated discrepancy submission).

v) Alert a radiologist after they hit "sign" on the radiology report that they have a potential miss. This may be provided in a generic way that does not show them where or what the pathology was, but only that they should review the images, in order to prevent bias.
vi) Flag a radiologist after they hit "sign" on a report that there is a potential miss for a specific pathology. This can be presented as, a) a text indicator only, b) a visual indicator in the viewer, including a mask over the suspicious areas on the right slices, or c) both.
vii) Automatically inform a radiologist of suspected condition/pathology upon opening the study.
viii) Show a radiologist a particular detected condition by overlaying a mask on the images.
ix) Provide data annotations produced by an AI model to classify reports, pull positives, identify areas of features, or outline features.

Other workflows and use cases enabled by the inference engine and AI model execution management include the following non-limiting use cases.

Use Case: Determining Pathology Presence on Radiology Report with NLP. After a radiologist signs a report, the report is sent to the inference engine to be classified as positive or negative by NLP models hosted in the inference engine (e.g., depicted in FIGS. 5 to 7). Once the classification is made, the result is sent back to the RIS to be stored as a question-answer key. This data, as well as other classifications done within the RIS itself by a report facilitator system, are used for measuring the performance of a model through sensitivity and specificity, discussed further below).

Use Case: Collecting Data on Image AI Model. An image AI model is containerized and plugged into the inference engine, as discussed above. As study messages are sent to the image router, they are retrieved and sent to the model if they are applicable to the model. From there, the model sends results to the image result router and the results are captured in the RIS. At this point, the data is not used, but only stored and measured. False Positives and False Negatives (e.g., determined after a complete evaluation by a radiologist) then may be identified and used for improving the image AI model. The results of the image AI model will be compared with NLP results to determine sensitivity and specificity of the image AI model.

Use Case: Prioritizing Studies on RIS Radiology Worklists. An image AI model that has been approved for use (e.g., approved based on safety qualifications) is used by the RIS to adjust prioritization of studies. The rules for prioritization are based on rules for "boosting" study prioritization for other purposes. If an image AI model predicts a likely positive condition, the study can be prioritized above non-emergent cases and above emergent cases; in various examples, this prioritization may remain a lower priority than critical studies (e.g., Stroke and Trauma protocol studies).

Use Case: Add to Radiologist QA Pool of Random Overreads. An image AI model can be used to seed the list of studies in a general radiologist "overread pool." These studies may form a pool of studies that are used by radiologists for quality assurance or validation. Any discrepancies noted in this overread process may be funneled to a QA review board or other review process. One example of this use case involves replacing some of the studies randomly chosen for overreads with studies having likely positive findings based on Image AI, to increase the likelihood of finding discrepancies from false negatives. For an image AI case to be flagged in this scenario, the Image AI would indicate "positive" whereas the NLP of the report would indicate "negative" for the condition. Another example of this use case involves selecting studies identified by the AI model as having a likely negative finding even as the NLP of the report indicates a positive finding, to increase the likelihood of finding a discrepancy from a false positive. Other methods may be used to track, perform QA review, and validate other disagreements between the AI model outcome and the NLP of the report.

Use Case: Automatically Submit AI Discrepancies to a QA review process. When an image AI model is positive and NLP is negative for a condition or pathology and the image AI model's specificity is above some level (e.g., 99%+), the case can be sent directly to a QA review process for further investigation review. This requires a high specificity because to prevent overloading the QA review process with false positives.

Use Case: Receive NLP and Image AI model feedback from QA. When a case is submitted as an automatic discrepancy to the QA review process, the QA review process can provide discrete answers regarding "Was the NLP correct?" and "was the Image AI correct" along with an area of free text to allow comments. This data will then be used to help tune models, pick better data sets for training, and understand where the AI or NLP analysis models are failing. This data also may be used for further verification, training, or reinforcement purposes.

Use Case: Alert Radiologist Technologist About Ordering Mistakes. Image AI models (e.g., X-ray Chest View-Type and the CT Anatomy Classifier) may be used to provide the radiologist technician with feedback about choosing the appropriate procedure(s) in the order management system. The result of the image AI model classification is passed to RIS, and the RIS then uses the information to ensure that the anatomy, view type, study type, and other information from the image AI model matches what the tech is ordering; if the match is not correct, the technician is informed and/or blocked from validating the study details.

Use Case: Automatically Create Radiologist Support Request If Order Mistake Detected. Image AI models such as the X-Ray Chest View-Type Detection and the CT Anatomy Classifier can determine certain pieces of information such as anatomy, view type, and study type that can check whether an order was ordered correctly or not. In scenarios where there is high certainty that the order does not match the images, a radiologist support request (or other technical support ticket) can be created automatically and the technician informed through an order management system.

Use Case: Alert the Radiologist if Case was Ordered Incorrectly. Image AI models such as the X-Ray Chest View-Type and the CT Anatomy Classifier can determine certain pieces of information such as anatomy, view type, and study type that can determine if the study data for the case does not indicate the correct procedures. This can impact billing and reporting, so the radiologist can be alerted to correct this information.

Use Case: Annotations from Radiologists. Radiologists can annotate studies for various Image AI use cases, based on suggested or predicted annotations. For instance, radiologists can log into a viewer application and see an annotation worklist of automated annotations (if they are configured). The radiologist can then use this information to classify reports and annotate images. The image annotations can be either purely geometric shapes (outlines) called ROI or the annotations may be segmentation level annotations. Use of segmentation annotation tool may include enabling the radiologist to threshold Hounsfield units and "paint" over the area they are segmenting.

Use Case: Save DICOM Object Outputs from Image AI Models to PACS. The Inference Engine and the use of Image AI models may be configured to support the output of various DICOM objects, including those produced by generative AI models. In addition, any web service APIs (e.g., with a PACS) can be configured to save the DICOM objects to the PACS study as a new series. Some of the DICOM Objects that may be saved include: Presentation State (PS) image data; Grayscale Presentation State (GSPS) image data; segmentation object data; structured reports (e.g., used for identifying a region of interest ROI); and the like.

Use Case: Incremental Annotations. Image AI model results may be used to provide structured reports (ROI) or segmentations that are accessible via the viewer during annotation workflows as a starting point. The radiologist should be able to "correct" the annotation and mark in the RIS whether the annotation was correct or not. The intent of this use case is to allow radiologists to spend less and less time annotating as AI models are trained to a higher degree of accuracy.

Use Case: Granular "Pick-List" Radiologists. Radiologists can choose to provide discrete, granular feedback that is designed purposefully to help with NLP and Image AI model building. This enables the platform to gather specific feedback data from radiologists. For instance, a UI may enable a radiologist to pick from a list of conditions/pathologies that is prepopulated by NLP of the report (they can uncheck), or to enables the radiologist to provide measurement information directly for specific pathologies.

Use Case: Radiologists Shown AI Results After Report Signing, with Query for Feedback. AI model results can be shown after signing the report, and the radiologist can be asked to provide feedback on the AI model outputs as "correct" or "incorrect," in a real world evidence setting. Such feedback may be in the form of binary (correct or incorrect) or scaled values (e.g., mostly correct, mostly incorrect, ranked on a percentage, etc.).

Use Case: Radiologists Shown AI Results Immediately Upon Case Open, with Query for Feedback. AI model results can be shown immediately upon opening the case and viewing the image, and the radiologist can be asked to provide feedback immediately whether the AI model output was correct or not. These suggested model results may be displayed as an overlay to the image, as a suggested value, as an annotation, or in other formats.

Use Case: Radiologists Shown AI Result "Overlays" in the Viewer, which can be Modified. AI model results may be provided as one or more overlays (SR, Segmentation Objects). A radiologist may be able to view this overlay, yet still be enable to "change" the overlay, or provide confirmation or rejection of the overlay, and save the accepted overlay to PACS in a new form of the immutable original. This accepted overlay may be used for subsequent study extraction to pull for re-training.

Use Case: Alert Hospital of Possible Critical Positive Findings. An AI model result that flags a study as positive with high sensitivity and specificity for critical findings can be used to immediately alert the referring physician, radiologist technician, or other emergent contact of the condition. This would be a multi-pronged communication—e.g., an order management system alert, an electronic message or text alert, a phone call (e.g., initiated using an outbound dialer), and the like.

Use Case: Detection of Endotracheal tube placement. Using a convolution neural network with annotations of Chest XR images, an AI model can be used to localize both the endotracheal tube and the carina on prospective Chest XR data. This information can be used to classify images as having a malpositioned tube or not, along with the distance in centimeters that the tube must be adjusted if malpositioned.

AI Model Validation and Governance

A challenge in the medical community regarding these and many other uses of AI is the "black box" nature of defining and measuring how a given AI model "works." The following validation and governance approaches provides an ability to automatically measure a model's performance and take action on it. The following validation and governance approaches also provides an architecture to run two or more models in parallel, to determine which model works the best and/or to run a 'new' version of a model for validation purposes while the currently approved model continues to run for other use cases.

In an example, verification may be integrated with the inference engine discussed above. In addition to image feature inferencing, the inference engine also runs NLP for report inferencing as well as collects data from other sources such as the RIS. This data is analyzed extensively, automatically, to calculate information such as the sensitivity and specificity of a model for given conditions or pathologies.

The analysis of output data provides an important perspective into the workings of an AI model itself by extensively measuring the output of the model with the input, to essentially "reverse engineer" what the model is doing. In various examples, this data collection is automated and acted upon by a system. For instance, if an AI model that is running drops out of pre-approved parameters, the model can automatically be removed from the system to prevent it from impacting other systems with data that does not meet the pre-approved quality metrics.

Although initial validation tests against AI models are designed to ensure that the models work as expected, there remains a need for model governance and monitoring on an ongoing basis. In particular, in platforms that analyze a large range of data, continual evaluation of model performance is imperative. In an example, model verification may involve the review, retrospectively, of one or more cohorts of data and then demonstrate the type of analysis and calculations performed on that data (including calculating sensitivity and specificity). This may be performed in scenarios to verify models perform correctly within specific workflow use cases, as well as to monitor those models on an ongoing basis to ensure that the model continues to meet approved thresholds.

In an example, the types of outcomes that may be observed from AI model verification may include: sensitivity, specificity, true positives, false positives, true negatives, false negatives, breakdown of urgencies (non-emergency, emergent, stroke/trauma), calculations for turn-around-time of studies read on the platform, among other metrics. Validation of retrospective data can occur using data already present in the medical imaging study databases, such as a comparison of the result of an AI model (e.g., which produces a positive or negative finding or a discrete classification, produced by a human) as well as the result of NLP run against the clinical radiology report (e.g., which indicates a positive and negative finding or a discrete classification, produced by a human).

Figure 9:
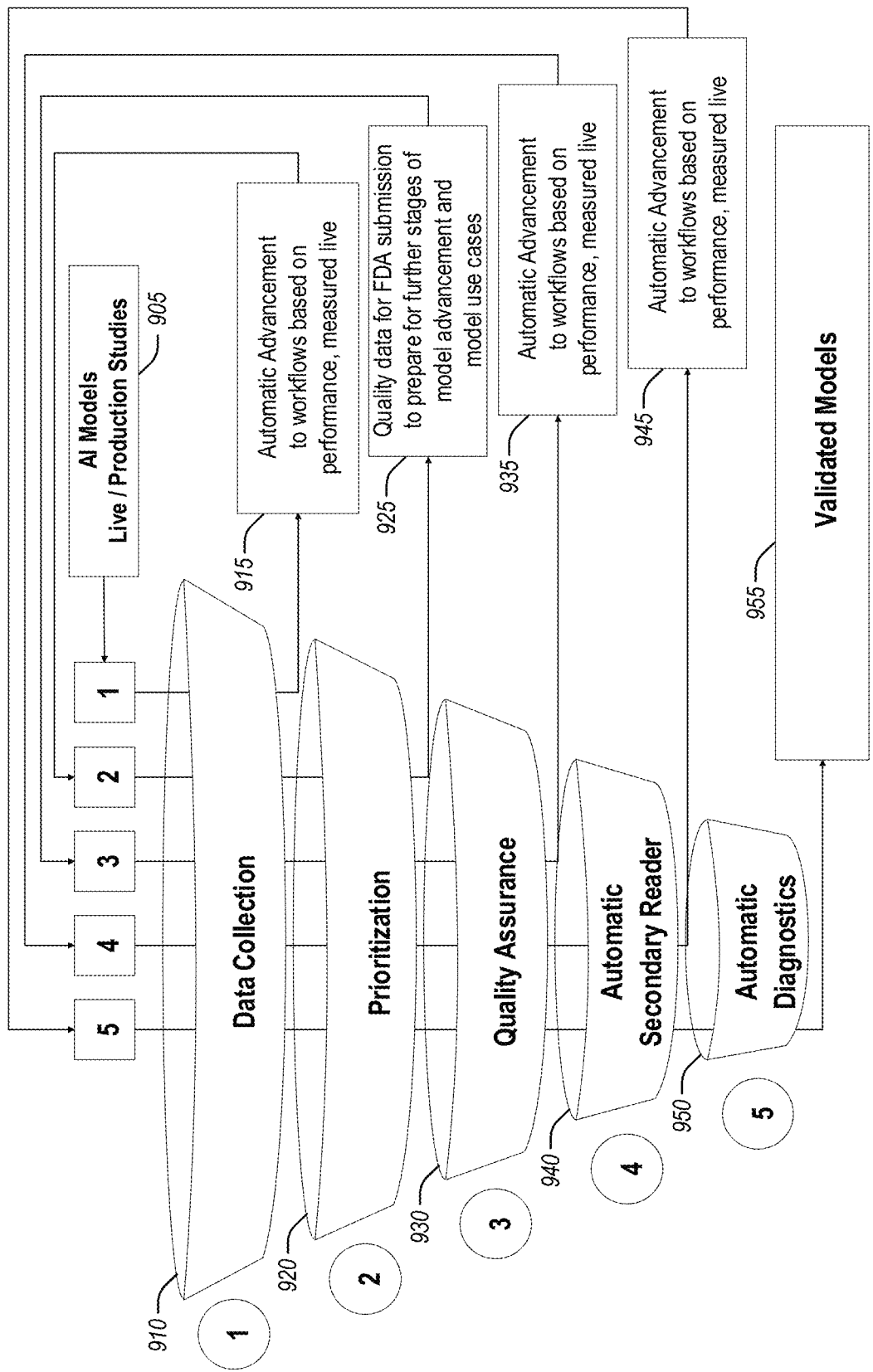
FIG. 9 illustrates an example medical imaging data processing use case which is assisted by the use of AI model operations, according to an example.

FIG. 9 illustrates an example medical imaging data processing use case which is assisted by the use of AI model operations. Here, a "funnel" of increasingly precise activities is provided for instances of AI models 905 that are used to evaluate live (production) imaging studies. As a model is used, refined, and validated at each stage (stages 910-950), the model may proceed for use within a later stage of analysis.

At an example first stage (stage 1, Data Collection 910), an AI model may be used for basic data collection activities. For example, at this stage, data 915 may be collected and verified from production (live) radiology studies using an AI model, to determine characteristics of studies within workflows. Data collection can be used to measure results of the AI model against NLP report outcomes, and to observe how the model works at scale, potentially without any clinical or workflow impacts.

At a second stage (stage 2, Prioritization 920), an AI model may be used to obtain data for basic workflow activities such as case prioritization, triage, worklist sorting, or other workflow changes. For example, at this stage, quality data 925 may be collected and verified for use with FDA submission or other validation purposes, to help demonstrate the characteristics of the AI model for more advanced activities. At this stage, data collection continues, and false positive and false negatives are tracked in an effort to provide improved training and reinforcement and increase the validity of the AI model.

At a third stage (stage 3, Quality Assurance 930), an AI model may be used to identify data characteristics, discrepancies, or cases which would benefit from quality assurance review. For example, at this stage, data 935 may be collected and verified for automatic advancement to QA workflows, based on the automated AI evaluation of production (live) use cases. The real world evidence and verification that is provided from QA workflows then can provide very accurate feedback for improvement and reinforcement of the AI model.

At a fourth stage (stage 4, Automatic Secondary Reading 940), an AI model may be used for more advanced activities, such as identifying data characteristics in a concurrent, secondary reading that is performed at the same time as a human radiology read. For example, at this stage, data 945 may be collected and verified for automatic advancement for use in specialized workflows, again based on the evaluation of production (live) use cases involving the model. Use cases involving automatic secondary reading may include identifying missed or probable error findings, image viewer tools and integration, and other automated actions. Real world evidence from production (live) use cases is still used to improve the model and its performance.

At a fifth stage (stage 5, Automatic Diagnostics 950), a model may be verified to perform actions as part of automatic diagnosis activities. This represents the most advanced type of activities, including those which have no human involvement. The validation of these operations may enable the use of a fully validated AI model 955 that is capable of performing any number of evaluative activities (including report data pre-population, correction, augmentation, etc.) in a radiology read setting.

In an example, analysis of individual AI models may involve a verification workflow, based on the evaluation of previously performed cases. For each evaluated case, there will be two main data points, the NLP result (true or false) and the Image AI Model result (true or false). The gold standard for this work will be the NLP. Natural Language Processing (NLP) is not 100% perfect in accuracy, however, for the purposes of this research the primary goal is governance and in order to provide governance at scale, NLP is used to enable us to measure model performance at scale. The research is designed to explore the governance process itself as a guideline for other organizations, therefore NLP will be used as gold-standard.

Based on the NLP and Image AI result, the following data elements can be calculated for each cohort:
  (i) Sensitivity
  (ii) Specificity
  (iii) False Positive Rate
  (iv) Condition Incidence Rate
  (v) True Positives
  (vi) True Negatives
  (vii) False Positives
  (viii) False Negatives Other workflow-specific data elements may also be calculated for each cohort. For instance, when attempting to analyze the result of a triage AI model for detecting emergent, non-emergent, or stroke/trauma conditions, the following data may be considered:
  (ix) Number of Emergent Cases that were Image AI Positive and NLP Positive
  (x) Number of Non Emergent Cases that were Image AI Positive and NLP Positive
  (xi) Number of Stroke/Trauma Cases that were Image AI Positive and NLP Positive
  (xii) Cases The sample size may be determined not to validate that a given model is precisely X and Y sensitivity and specificity, but rather attempting to ascertain the risk scenarios for worklist prioritization given a model's behavior.

Figure 10:
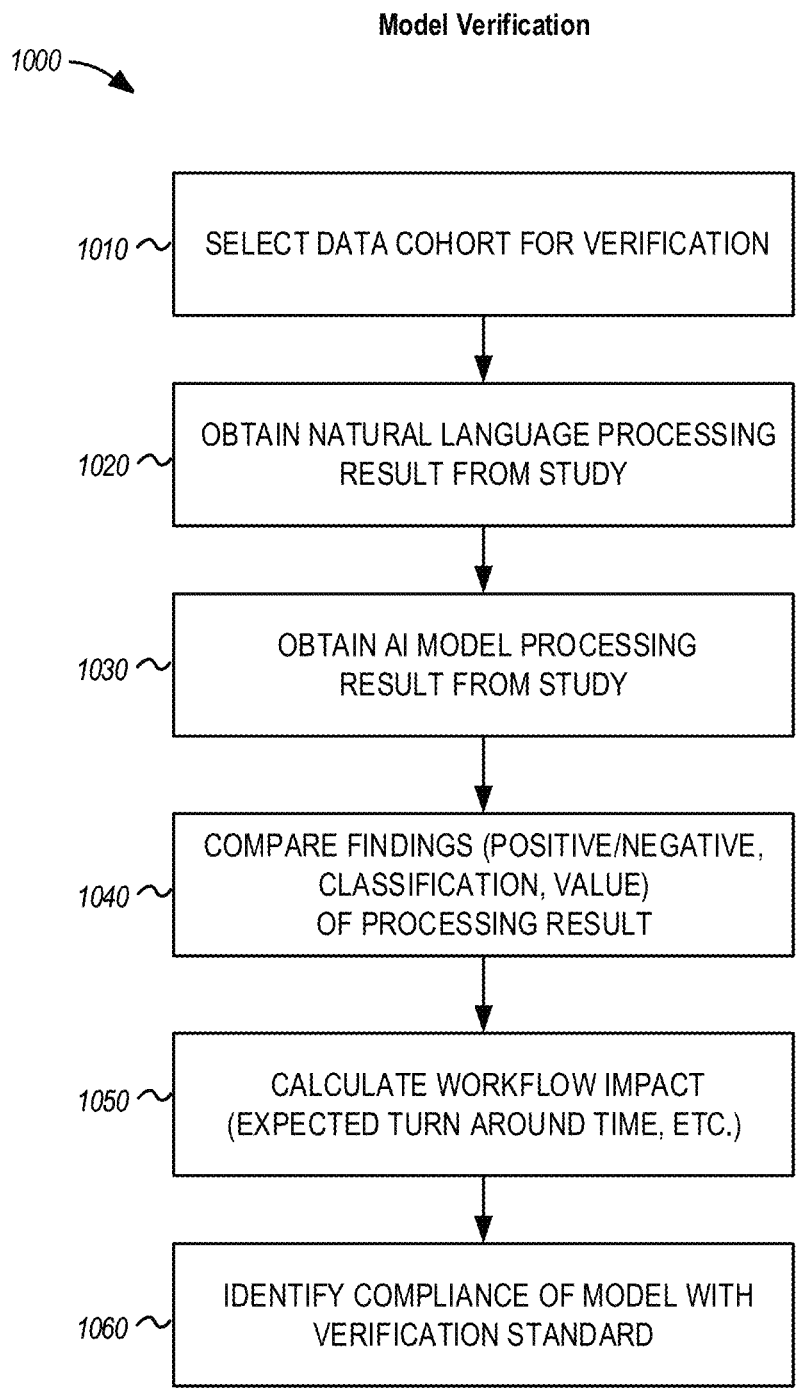
FIG. 10 illustrates a flowchart of example model verification operations performed for processing data of a medical study, according to an example.

FIG. 10 illustrates a flowchart 1000 a model verification operations performed for processing data of a medical study, based on these approaches for data analysis. It will be understood that the verification processes depicted in the flowchart 1000 may be used in connection with the stages depicted in FIG. 9, and based on data produced with the workflows and inference engine described within discussion of FIGS. 5 to 8.

At operation 1010, the process for verification may include the selection of a data cohort. This data cohort may be provided from prior studies of a plurality of human subjects which meet some selection criteria. The process for verification then proceeds with obtaining the processing results from the prior studies (e.g., provided by the data cohort). This may include, at operation 1020, obtaining an NLP result from each study (e.g., based on NLP text analysis of a radiologist report) and at operation 1030, obtaining an AI model processing result from each study (e.g., an outcome or output produced from an AI model analysis of a set of images from the study).

At operation 1040, the findings indicated by the NLP result are compared with the AI model processing result, such as through a comparison of a positive or negative finding, a classification or detected property, a detected or predicted value, and the like. Additionally, at operation 1050, the workflow impact of the processing result from the AI model (such as effects on turnaround time, worklist prioritization) is also calculated.

The process for verification concludes with an identification of the compliance of the AI model outputs with one or more aspects of a verification standard (operation 1060). For example, the verification standard may indicate a maximum workflow impact, and a maximum of false negative or false positive findings. Based on these compliance results, a model may be replaced, identified for further training, promoted, placed into production, taken out of production, and the like.

When combined with continual monitoring of models to ensure compliance, these and similar verification processes may be enabled in a radiology processing platform for: automated alerting of non-compliant models; automated removal of non-compliant models from production workflows; monitoring performance to evaluate impact to workflows, to alert or remove models based on disproportionate effects; and the like. Additionally, multiple versions of models may be executed side by side to ensure compliance of an updated or modified model, and automated graduation of the updated or modified model once compliance is proven.

Figure 11:
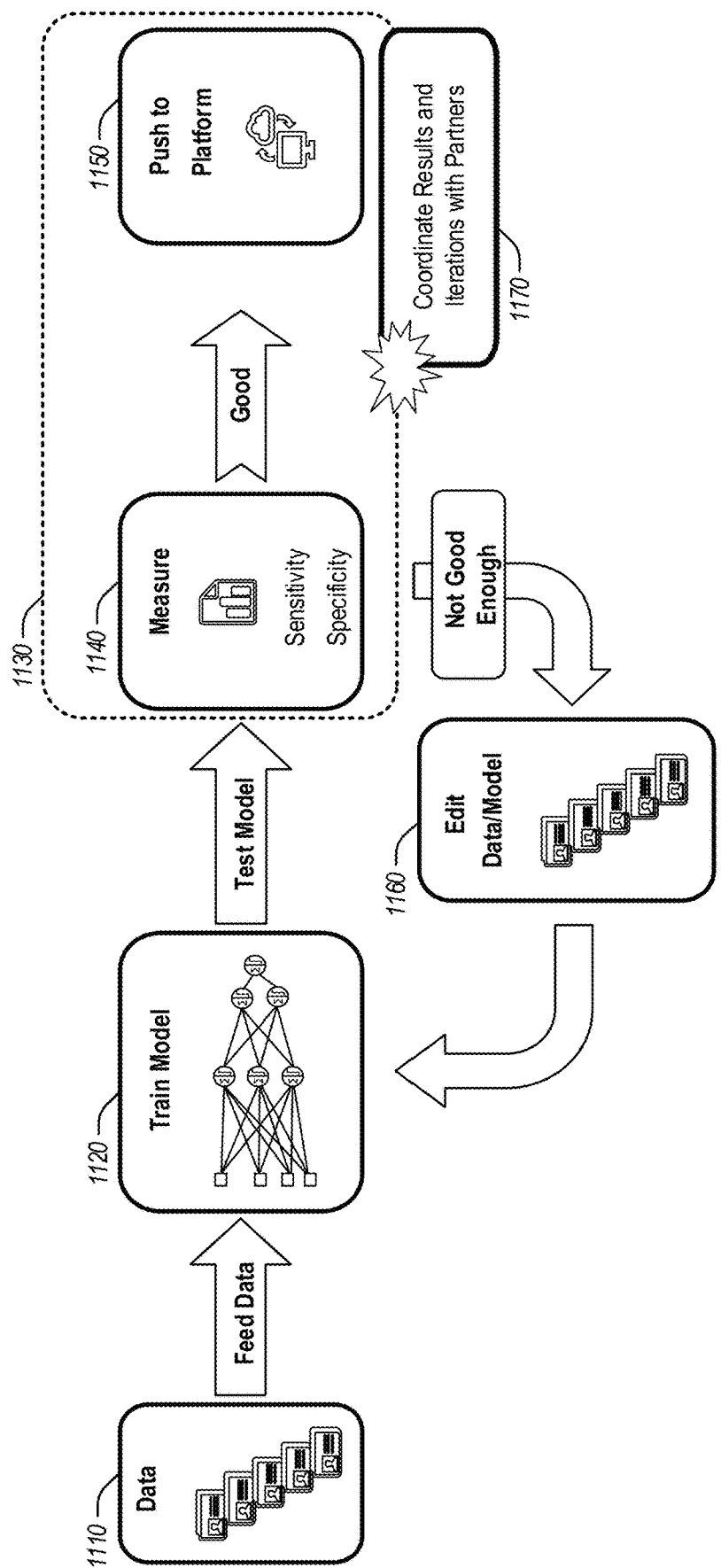
FIG. 11 illustrates an example model deployment use case which is assisted by the use of AI model verification, according to an example.

FIG. 11 illustrates an example model deployment use case which is assisted by the use of AI model verification. It will be understood that this use case provides a simplified example of how the operations of FIG. 10 can be applied with model training, verification, measurement, and deployment; additional steps discussed throughout this document are not depicted for simplicity.

Within the model deployment use case, study data 1110 is used to train at least one AI model 1120. This trained model is tested within a verification process 1130, which tests output, performance, and effects of the AI model. In an example, the verification process 1130 performs measurement 1140 of sensitivity and specificity of the model; if the measurement 1140 meets requirements or defined thresholds, then the verification process 1130 deploys the AI model for use in a platform 1150. If the measurement 1140 does not meet requirements or defined thresholds, then the data or model inputs are edited 1160, to cause re-training, reinforcement, and an updated version of the model.

A verification process may be employed to confirm the efficacy of an AI model in a radiology evaluation workflow to automatically detect certain medical conditions. Among other examples, such verification may be used for verifying worklist prioritization for critical, acute positive pathologies such as intracranial hemorrhage (ICH), pulmonary embolism (PE), pneumothorax, aortic dissection, and pneumoperitoneum. It will be understood that these conditions are particularly time sensitive; thus, accuracy in the model to prevent false negatives may be extremely important.

The use of NLP result as a gold-standard against image AI model output may be employed in a model governance process for a worklist prioritization model, to determine the rate of false positives and true positives, and the "overall boost" to prioritization and the risk to non-prioritized studies. Thus, in some scenarios, the error rate or accuracy of our measurement itself may not be the primary measurement, as instead the effects on the workflow (and the risk to the workflow of whether or not the model is accurate) are measured. Thus, when evaluating a triage AI model, an important metric involved is the total number of studies boosted (prioritized)—produced from the sum of the false positives and true positives from the model. This risk is then weighed against the sensitivity of the model—since the sensitivity should not be zero.

A sample size of the data cohort may be selected based on stabilized results and the rate of change while averaging over longer periods of time, to obtain a consistent average for both sensitivity and specificity. This sample size should be selected while considering that, most medical conditions detected with Image AI may have a very low incidence rate (e.g., 2-5% occurrence rate). Because of this, specificity will stabilize very quickly with volume (there are way more negatives) but sensitivity may need monitoring.

Radiology System Operational Examples

The previously described approaches for workflow enhancement, model execution management, and model verification may be implemented in a variety of settings and operational scenarios. These approaches may be integrated into the following operational examples and system arrangements of FIGS. 12 to 15.

Figure 12:
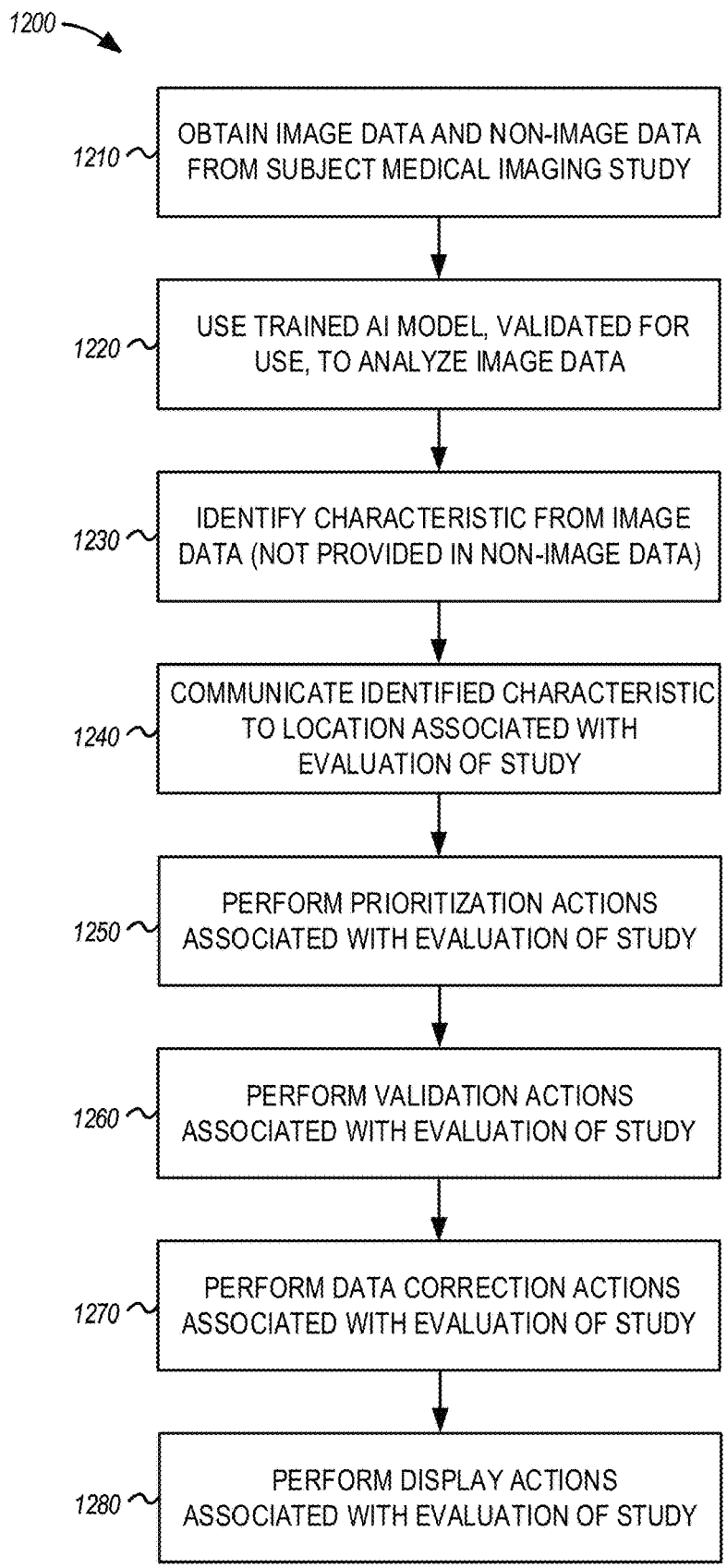
FIG. 12 illustrates a flowchart of example operations for medical data processing, based on AI-assisted workflow management, inferencing engine management, and validation and governance management techniques, according to an example.

FIG. 12 illustrates a flowchart 1200 of an example workflow for processing data of a medical study, based on AI-assisted workflow management, inferencing engine management, and validation and governance management techniques. The particular sequence depicted in the flowchart 1200 is illustrated to integrate the features of the management approaches discussed in among FIGS. 3 to 11, such as during a workflow responsible for processing of radiology images and orders. However, it will be understood that the sequence of operations may vary depending on the precise data operations to be performed upon the study data produced by the imaging procedure and the originating medical facility, the conditions present when evaluating the study data, the state of the study data (including the number of errors or discrepancies in the study data), and human actions used to effect the workflow.

An initial operation for the flowchart 1200 may involve obtaining image data and non-image data from a subject medical imaging study (operation 1210), such as in a radiology workflow discussed above. For instance, the image data (e.g., DICOM image data) and the non-image data (e.g., radiology order data) may be provided from a radiological imaging procedure, as the medical imaging study corresponds to a radiological read request for diagnostic evaluation of the image data by a medical professional evaluator (e.g., radiologist).

The flowchart 1200 continues with the use of at least one trained AI model, to analyze image data (operation 1220). One or more characteristics that is provided by the non-image data may be used to select a particular trained AI model from among a plurality of trained AI models. Although not depicted, a selection process may be used to identify the appropriate AI model to use in an analysis workflow, based on non-image data or even characteristics of the image data itself.

The governance process discussed herein be used to modify or monitor usage and results of the AI model. For instance, a governance process may validate that the AI model is suitable to identify at least one particular characteristic according to a defined governance standard. In the various examples suggested above, the governance process may be used to set specificity and sensitivity goals. For instance, the defined governance standard may establish a specificity and sensitivity to identify the particular characteristic, with the AI model. The defined governance standard may also identify if AI model cannot be used, such as if accuracy dips below a certain threshold.

The specificity and sensitivity of a governance standard may be established based on validating this identification characteristic for multiple medical imaging studies performed for multiple human subjects. However, other considerations or criterion may also be used. For instance, the specific AI model may be validated based on an identification of the particular characteristic, and a comparison of results identified by NLP in study reports and results identified by the trained AI model. In other words, the accuracy of the model may be calculated by comparing NLP results to AI results, in settings involving a large volume of test data.

The flowchart 1200 continues with use of the AI model to produce an output, that identifies the characteristic from image data (with this characteristic not being provided or indicated in the non-image data) (operation 1230). This characteristic may relate to: priority of the medical imaging study; characteristics of a medical imaging procedure used to capture the image data; at least one anatomical feature represented in the image data; at least one medical condition represented in the image data; or other characteristics discussed in the use cases above. This identified characteristic then can be communicated to a location associated with an evaluation of study (operation 1240), such as to a radiologist workstation, a RIS or PACS system, another AI model, a health information system, or any of the other systems suggested herein.

Based on the AI-identified characteristics, one or more prioritization, validation, correction, or display actions may be performed (operations 1250-1280). These actions may occur as part of an evaluative workflow (e.g., as part of control of a radiology read workflow) or as part of other data collection and validation activities. In a radiology read workflow, additional operations may be integrated with radiology report actions and validations, such as with an processing workflow that compares image AI findings to NLP findings as follows: (a) receive report data provided from a radiologist evaluation; (b) use at least one NLP model (e.g., an AI model), trained for NLP analysis, to analyze the report data; (c) identify the particular characteristic in the report data, based on output from the NLP model trained for NLP analysis; and (d) determine at least one evaluation action, based on a comparison or difference between the particular characteristic identified by the NLP model from the report data and a characteristic identified by the AI model from the image data.

Operations that perform prioritization actions (operation 1250) may prioritize a worklist, trigger notifications, prioritize report delivery, among other aspects discussed above. For example, such actions may include: adding or prioritizing of an assignment of a radiology study in a radiologist worklist; providing a notification of an emergent or critical finding to a medical facility that is the source of the medical imaging study; or prioritizing results and reporting for the radiology study, within a workflow or other systems.

Operations that perform validation actions (operation 1260) may perform any of the governance or alert functions discussed above. For example, such actions may include: validation of data in the non-imaging data; identification of discrepancies between characteristics detected in the imaging data and indicated in the non-imaging data; adding the medical imaging study to a quality assurance workflow; or adding the medical imaging study to a second read workflow (e.g., for reading by multiple radiologists).

Operations that perform data correction actions (operation 1270) may perform actions to modify, update, or suggest changes to data. For example, such actions may include: performing corrective actions to the non-imaging data; performing corrective actions to the imaging data or the display or visualization of the imaging data; or performing corrective actions to a report (radiology report) associated with the medical imaging study.

Operations that perform display actions (operation 1280) may involve the display, visualization, or suggestion of AI-detected findings, changes to image displays (e.g., hanging protocols, highlighting pathology, etc.), auto-correction of report dictation, among other aspects. For example, such actions may include: providing an indication of the identified particular characteristic to an evaluator of the medical imaging study (a radiologist); changing a display of the imaging data at a display of an evaluator of the medical imaging study (a radiologist display); or changing a report prepared at a display of an evaluator of the medical imaging study (a radiologist display).

Although the flowchart 1200 was discussed above from the perspective of one AI model, it will be understood that arrangements involving multiple AI models may be used; for example, in scenarios where output from a first trained AI model is used as an input to a second trained AI model; or where AI models operate in a parallel with each other, including with uses of a beta and production AI model, running in parallel for validation or governance purposes. Additionally, use of multiple models may encompass executing at least a first AI model on a portion of the image data at an on-premise computing location, and causing execution of at least a second AI model on a portion of the image data at an off-premise computing location. Other variations involving the use of production versus testing models, or use of the inference engine architecture discussed above, may also be implemented.

Additionally, use of multiple models may encompass using at least one other trained AI model to analyze the image data and the non-image data, such as for sending data to multiple AI models to identify multiple things. When multiple models are used, a value of the particular characteristic identified by the trained AI model may differ from a value of the particular characteristic identified by the other trained AI model; many of the corrective, validation, or quality assurance actions noted above may be taken in response to such different values.

Figure 13:
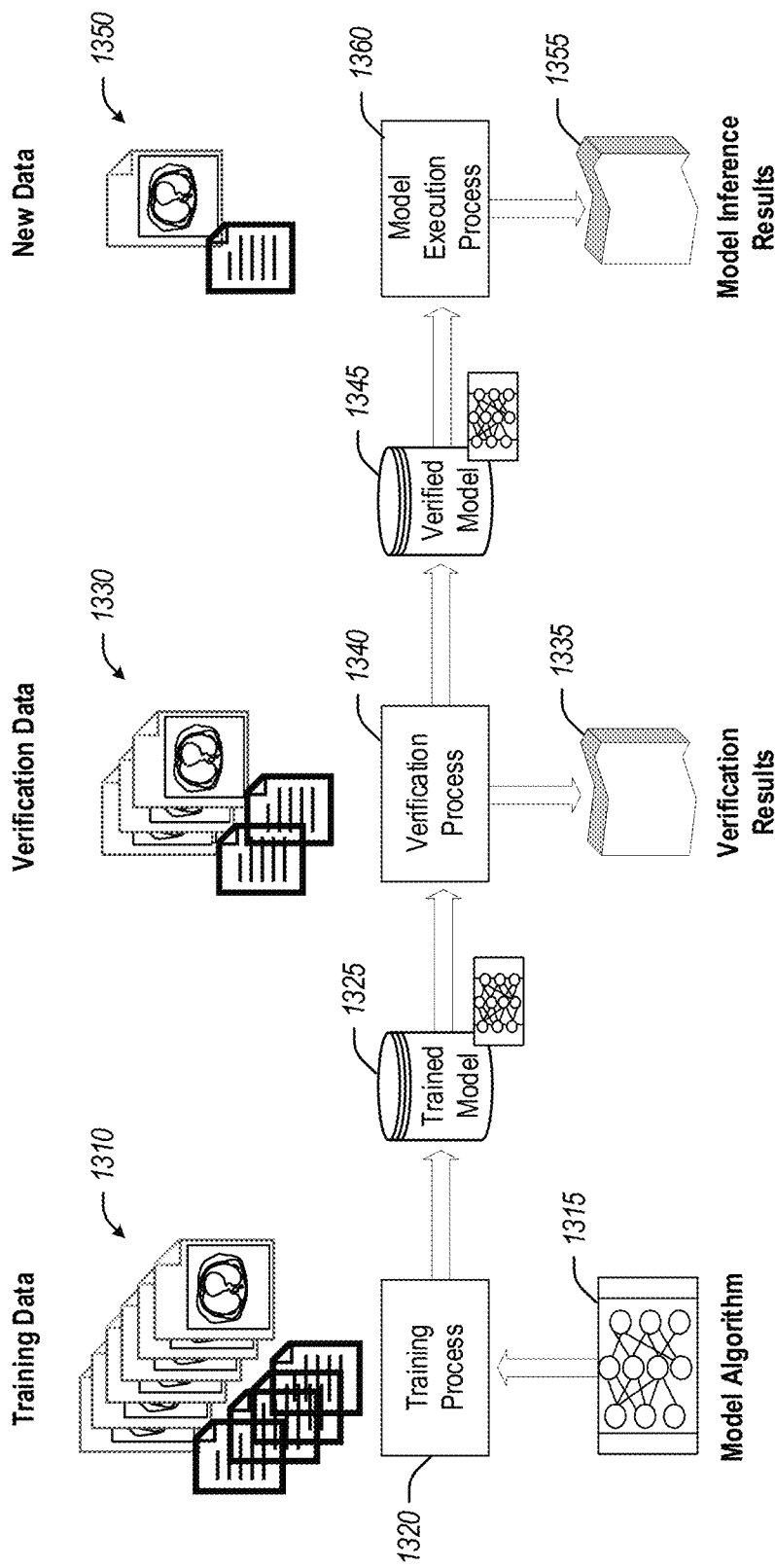
FIG. 13 illustrates a workflow for training, verifying, and operating an AI model with medical imaging data use cases, according to an example.

FIG. 13 illustrates an example arrangement of a system that can be used to train, validate, and operate an AI model, such as an AI model to classify data, generate inferences, perform regression, produce predictions or labels, or otherwise produce outputs from a data input. As shown, a trained AI model 1325 may be produced from a training process 1320. This training process may receive a set of classified training data 1310 which is provided as input to the training process, to operate on a model algorithm 1315 to adjust the weights, values, or properties used within the model algorithm as part of a learning procedure. This model algorithm 1315 may include any of the types of AI algorithms or arrangements discussed herein, and involve unsupervised, supervised, or reinforcement learning approaches as part of training operations.

As an example, the classified training data 1310 may include image data that represents one or more objects (e.g., anatomical objects), with each image also including or being associated with a label, metadata, classification, or similar informative data. The classified training data 1310 may also include other formats of medical data in addition to the imaging data. Thus, a trained model 1325 may not be limited to image analysis but may encompass some combination of images, text, data values, etc.

The trained model 1325 is provided to a verification process 1340, which produces verification results 1335 from a set of verification data 1330. For instance, the verification process may follow the approaches discussed in FIGS. 9 to 11 for model verification, to ensure compliance of a trained model with some specification. It will be understood that other forms of evaluation and verification, reinforcement, and adaptive learning may also be performed with use of the verification results 1335.

Upon completion of the verification process, the trained model 1325 is now identified as a verified model 1345, for use within a model execution process 1360. The model execution process 1360 is used to operate the AI model upon a set of new data 1350, such as new imaging and order data obtained from a human subject during a medical imaging procedure as discussed above. The model execution process 1360 is used to produce model inference results 1355, which may take any of the forms (e.g., classifications, labels, values, annotations, identified pixels, generative data) discussed above.

Figure 14:
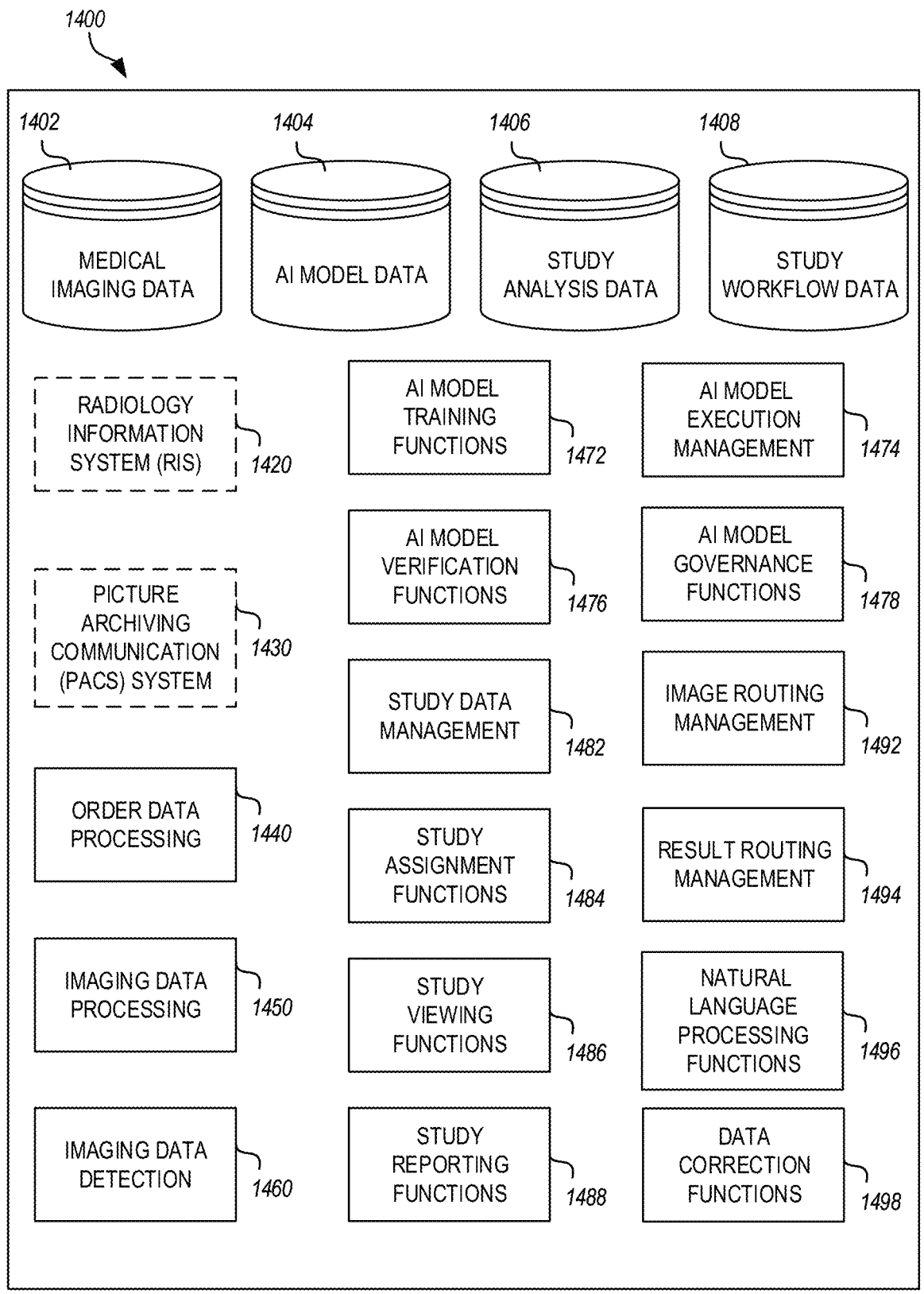
FIG. 14 illustrates a configuration of a computing system arranged to process medical imaging data, according to an example.

FIG. 14 illustrates an example configuration of a system architecture 1400 configured to implement the presently described processing system according to an example described herein. System architecture 1400 may implement components such as the workflow processing system 102 and features of the image evaluation system 106, the data processing system 108, and aspects of the platform 420. The system architecture 1400 may include features of a radiology information system 1420, a picture archiving communication system 1430, order data processing 1440, image data processing 1450, image data detection 1460, AI model training 1472, AI model execution management 1474, AI model verification functions 1476, AI model governance functions 1478, study data management 1482, study assignment functions 1484, study viewing functions 1486, study reporting functions 1488, image routing management 1492, result routing management 1494, natural language processing functions 1496, and data correction functions 1498. In operation with these features, the system architecture 1400 may further include a plurality of databases or data stores, including a medical imaging database 1402, an AI model database 1404, a study analysis database 1406, and a study workflow database 1408. Such features may be embodied by any number of software or hardware forms (including through the use of physical or logical blocks of computer instructions, which may, for instance, be organized as an object, procedure, or function).

The medical imaging database 1402 may provide a location for storage of imaging data (and metadata) for medical imaging procedures and associated studies. The machine learning model database 1404 may provide a location for storage of deep learning models, inputs, and relevant parameters for operation of the machine learning algorithms. The study analysis database 1406 may provide a location for storage of information for study evaluation states of particular studies, preferences for study evaluations, and other data fields used to assist the study evaluation in response to the performance of the machine learning models. The study workflow database 1408 may provide a location for storage of information for workflow states of particular studies, preferences for workflow operations, and other data fields used to assist the workflow operations occurring in response to the performance of the machine learning models.

The respective features of the system architecture 1400 may perform functional operations to effect the processing, image identification, and workflow management techniques described herein. For example, the radiology information system 1420 may be used to provide respective information processing functions of a RIS. The picture archiving communication system 1430 may be used to provide image storage and access features of a Picture Archiving Communication System (PACS). The order data processing 1440 may be used to process orders, and determine relevant information for non-image data of studies. The image data processing 1450 may be used to request, receive, validate, and store images data of studies.

The image data processing 1450 may be used to perform imaging processing operations on imaging data obtained from a set of data associated with a medical imaging procedure, or from a customer imaging device, an image archive, medical facility data store, or other imaging data source, such as with processing operations that provide image data as input to the machine learning models. The image data detection 1460 may be used to implement the machine learning model, such as with performance of a deep learning model to detect certain medical conditions within the images of the study image data.

The AI model training functions 1472 may be used to implement training of the AI model, such as with the use of imaging and non-imaging data completed by previous study evaluations. The AI model execution management 1474 may be used to invoke AI model outputs within workflows, as discussed above. The AI model verification functions 1476 may be used to compare results of the image detection operations with results of the study evaluations, and to modify the machine learning model based on verification of outcomes, as discussed above. Finally, the AI model governance functions 1478 may be used to control or modify the use of AI model operations within workflow operations, as discussed above.

The study data management 1482 may be used to coordinate the transmission and transfer of image and non-image data associated with an imaging study based on the results of the image detection operations and the adjusted workflows. The study assignment functions 1484 may be used to provide assignments to one or more evaluators (and to facilitate the transfer of data to computing systems associated with the one or more evaluators) based on the results of the image detection operations and the adjusted workflows. The study viewing functions 1486 may be used to view studies (and specific types of rendering data) on screen by an evaluating user, which may be influenced by the detection of certain medical conditions, prioritization, or other results of the image detection operations and the adjusted workflows. The study reporting functions 1488 may be used to establish reporting functions for the evaluating user, from report information that is created or contributed to by the evaluating user, with such report information being influenced or assisted by the results of the image detection operations and the adjusted workflows.

Additional processing functions include image routing management 1492 and result routing management 1494, such as may be used within an inference engine platform to process images and obtain results, as discussed above; natural language processing functions 1496 to obtain useful information and metadata from text in study reports; and data correction functions 1498 to correct or modify image metadata. Additional functions and components, not shown in FIG. 14, may be provided to implement the data processing provided within the inference engine architectures of FIGS. 5 to 7, the workflow enhancement and management features of FIGS. 8 to 9, and model verification features of FIGS. 10 to 11, and accompanying text.

Figure 15:
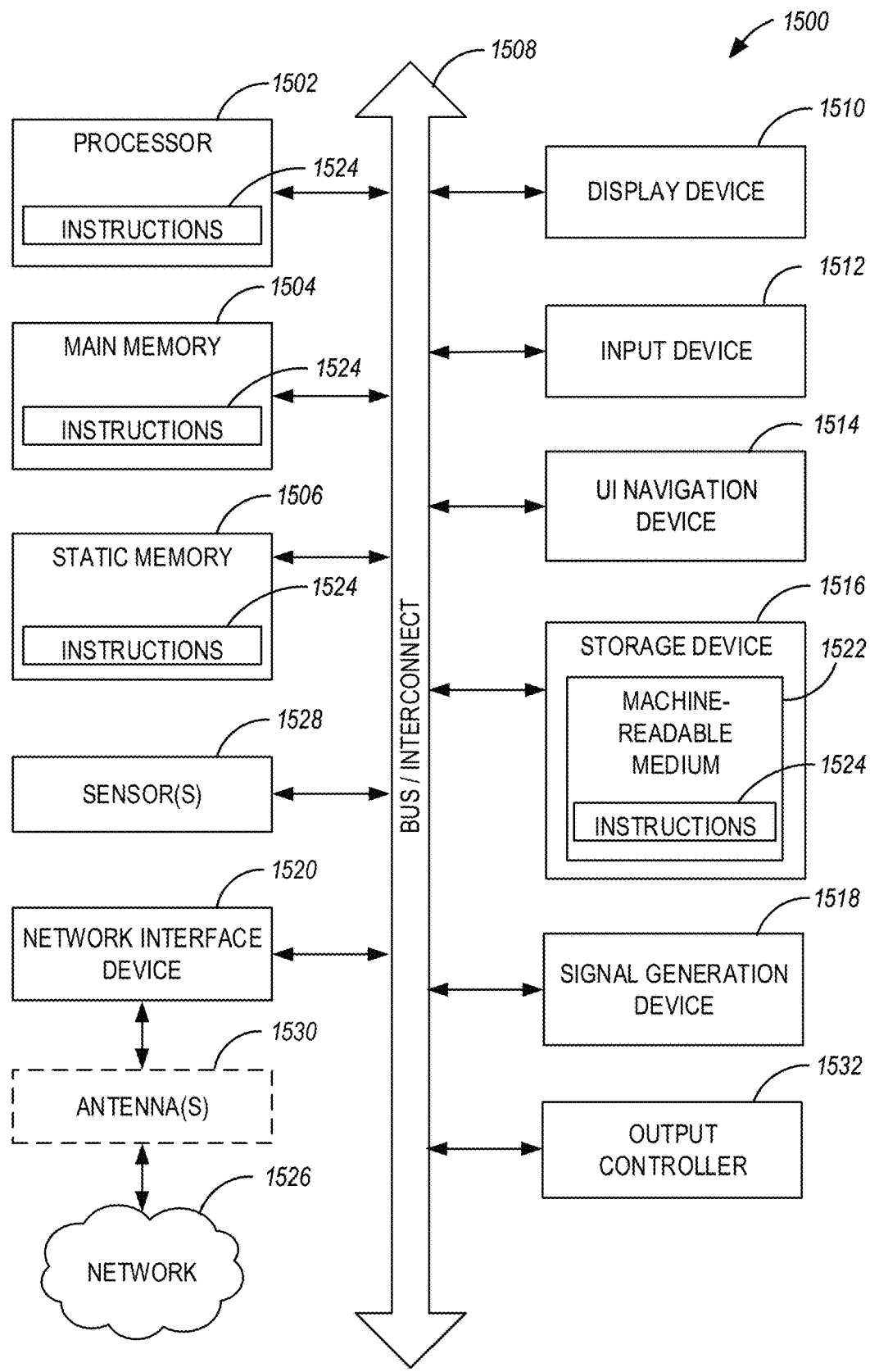
FIG. 15 illustrates an example of a machine configured to perform computing operations, according to an example.

FIG. 15 is a block diagram illustrating an example computing system 1500 upon which any one or more of the methodologies herein discussed may be run according to an example described herein. Computer system 1500 may be embodied as a computing device, providing operations of the components featured in the various figures, including components of the workflow processing system 102, the imaging system 104, the image evaluation system 106, the data processing system 108, components and data storage elements in system architecture 1400, platform 420, or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1500 includes a processor 1502 (e.g., a central processing unit (CPU), a graphics processing unit (GPU) or both), a main memory 1504 and a static memory 1506, which communicate with each other via an interconnect 1508 (e.g., a link, a bus, etc.). The computer system 1500 may further include a video display unit 1510, an alphanumeric input device 1512 (e.g., a keyboard), and a user interface (UI) navigation device 1514 (e.g., a mouse). In one embodiment, the video display unit 1510, input device 1512 and UI navigation device 1514 are a touch screen display. The computer system 1500 may additionally include a storage device 1516 (e.g., a drive unit), a signal generation device 1518 (e.g., a speaker), an output controller 1532, and a network interface device 1520 (which may include or operably communicate with one or more antennas 1530, transceivers, or other wireless communications hardware), and one or more sensors 1528.

The storage device 1516 includes a machine-readable medium 1522 on which is stored one or more sets of data structures and instructions 1524 (e.g., software) embodying or utilized by any one or more of the methodologies or functions described herein. The instructions 1524 may also reside, completely or at least partially, within the main memory 1504, static memory 1506, and/or within the processor 1502 during execution thereof by the computer system 1500, with the main memory 1504, static memory 1506, and the processor 1502 constituting machine-readable media.

While the machine-readable medium 1522 is illustrated in an example embodiment to be a single medium, the term "machine-readable medium" may include a single medium or multiple media (e.g., a centralized or distributed database, and/or associated caches and servers) that store the one or more instructions 1524. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of non-transitory machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the features in the system architecture 1400 of the processing system may be client-operated software or be embodied on a server at a cloud, edge, or intermediate location, running an operating system with software, virtual machines, containers, or the like running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, features, or mechanisms. Such items are tangible entities (e.g., hardware) capable of performing specified operations and may be configured or arranged in a certain manner. In an example, circuits may be arranged (e.g., internally or with respect to external entities such as other circuits) in a specified manner as a module, component, or feature. In an example, the whole or part of one or more computer systems (e.g., a standalone, client or server computer system) or one or more hardware processors may be configured by firmware or software (e.g., instructions, an application portion, or an application) as an item that operates to perform specified operations. In an example, the software may reside on a machine readable medium. In an example, the software, when executed by underlying hardware, causes the hardware to perform the specified operations.

Accordingly, such modules, components, and features are understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules, components, and features are temporarily configured, each of the items need not be instantiated at any one moment in time. For example, where the modules, components, and features comprise a general-purpose hardware processor configured using software, the general-purpose hardware processor may be configured as respective different items at different times. Software may accordingly configure a hardware processor, for example, to constitute a particular item at one instance of time and to constitute a different item at a different instance of time.

Additional examples of the presently described method, system, and device embodiments are suggested according to the structures and techniques described herein. Other non-limiting examples may be configured to operate separately, or can be combined in any permutation or combination with any one or more of the other examples provided above or throughout the present disclosure.

What is claimed is:

1. A method of processing data in a medical evaluation workflow, performed with electronic operations executed with a processor of a computing device, the electronic operations comprising:
   obtaining image data and non-image data associated with a medical imaging study for a human subject;
   using at least one trained artificial intelligence (AI) model to analyze the image data, wherein the trained AI model is validated with a defined governance standard to identify at least one particular characteristic;
   identifying the particular characteristic in the image data, based on output from the trained AI model, wherein the identified particular characteristic is not indicated by the non-image data; and
   communicating the identified particular characteristic to a location associated with evaluation of the medical imaging study, wherein the identified particular characteristic controls at least one automated medical image data processing action at the location associated with evaluation.

2. The method of claim 1, wherein the defined governance standard establishes a specificity and sensitivity to identify the particular characteristic within multiple medical imaging studies performed for multiple human subjects.

3. The method of claim 2, wherein the trained AI model is validated based on a verified identification of the particular characteristic, using a comparison of results identified by natural language processing in study reports and results identified by the trained AI model, the study reports and results being performed on the multiple medical imaging studies performed for the multiple human subjects.

4. The method of claim 1, wherein using the trained AI model includes use of multiple trained AI models, wherein output from a first trained AI model is used as an input to a second trained AI model.

5. The method of claim 1, wherein using the trained AI model to analyze the image data comprises causing execution of at least a first AI model on a portion of the image data at an on-premise computing location, and causing execution of at least a second AI model on a portion of the image data at an off-premise computing location.

6. The method of claim 1, the electronic operations further comprising:
   selecting the trained AI model from among a plurality of trained AI models, based on at least one characteristic indicated in the non-image data.

7. The method of claim 1, the electronic operations further comprising:
   using at least one other trained AI model to analyze the image data and the non-image data, wherein a value of the particular characteristic identified by the trained AI model differs from a value of the particular characteristic identified by the other trained AI model.

8. The method of claim 1, the electronic operations further comprising:
   receiving report data provided from evaluation of the medical imaging study;
   using at least one AI model, trained for analysis of natural language processing, to analyze the report data;
   identifying the particular characteristic in the report data, based on output from the AI model trained for analysis of natural language processing; and
   determining at least one evaluation action based on the identifying of the particular characteristic from the report data and the identifying of the particular characteristic from the image data.

9. The method of claim 1, wherein the identified particular characteristic relates to at least one of:
   priority of the medical imaging study;
   characteristics of a medical imaging procedure used to capture the image data;
   at least one anatomical feature represented in the image data; or
   at least one medical condition represented in the image data.

10. The method of claim 1, wherein communicating the identified particular characteristic to a location associated with evaluation causes at least one prioritization action, including at least one of:
    adding or prioritizing of an assignment of the medical imaging study in a worklist;
    providing a notification of an emergent or critical finding to a source of the medical imaging study; or
    prioritizing results and reporting for the medical imaging study.

11. The method of claim 1, wherein communicating the identified particular characteristic to a location associated with evaluation causes at least one validation action, including at least one of:
    validation of data in the non-image data;
    identification of discrepancies between characteristics detected in the image data and indicated in the non-image data;
    adding the medical imaging study to a quality assurance workflow; or
    adding the medical imaging study to a second read workflow.

12. The method of claim 1, wherein communicating the identified particular characteristic to a location associated with evaluation causes at least one corrective action, including at least one of:
    performing corrective actions to the non-image data; or
    performing corrective actions to a report associated with the medical imaging study.

13. The method of claim 1, wherein communicating the identified particular characteristic to a location associated with evaluation causes at least one display action, including at least one of:
    providing an indication of the identified particular characteristic to an evaluator of the medical imaging study;
    changing a display of the image data at a display of an evaluator of the medical imaging study; or
    changing a report prepared at a display of an evaluator of the medical imaging study.

14. The method of claim 1, wherein the image data is provided from a radiological imaging procedure, wherein the non-image data is provided from a radiological imaging order, and wherein the medical imaging study corresponds to a radiological read request for diagnostic evaluation of the image data by a medical professional evaluator, the radiological read request indicated by the radiological imaging order.

15. The method of claim 1, wherein the trained AI model is a: machine learning model or convolutional neural network.

16. A non-transitory machine-readable storage medium, the machine-readable storage medium comprising instructions that, when executed by a processor of a computing device, causes the computing device to perform operations comprising:
- obtaining image data and non-image data associated with a medical imaging study for a human subject;
- using at least one trained artificial intelligence (AI) model to analyze the image data, wherein the trained AI model is validated with a defined governance standard to identify at least one particular characteristic;
- identifying the particular characteristic in the image data, based on output from the trained AI model, wherein the identified particular characteristic is not indicated by the non-image data; and
- communicating the identified particular characteristic to a location associated with evaluation of the medical imaging study, wherein the identified particular characteristic controls at least one automated medical image data processing action at the location associated with evaluation.

17. The machine-readable storage medium of claim 16,
- wherein the defined governance standard establishes a specificity and sensitivity to identify the particular characteristic within multiple medical imaging studies performed for multiple human subjects,
- wherein the trained AI model is validated based on a verified identification of the particular characteristic, using a comparison of results identified by natural language processing in study reports and results identified by the trained AI model, the study reports and results being performed on the multiple medical imaging studies performed for the multiple human subjects.

18. The machine-readable storage medium of claim 16, the instructions further to cause the computing device to perform operations comprising:
- receiving report data provided from evaluation of the medical imaging study;
- using at least one AI model, trained for analysis of natural language processing, to analyze the report data;
- identifying the particular characteristic in the report data, based on output from the AI model trained for analysis of natural language processing; and
- determining at least one evaluation action based on the identifying of the particular characteristic from the report data and the identifying of the particular characteristic from the image data.

19. The machine-readable storage medium of claim 16, wherein communicating the identified particular characteristic to a location associated with evaluation causes at least one prioritization action, including at least one of:
- adding or prioritizing of an assignment of the medical imaging study in a worklist;
- providing a notification of an emergent or critical finding to a source of the medical imaging study; or
- prioritizing results and reporting for the medical imaging study.

20. The machine-readable storage medium of claim 16, wherein communicating the identified particular characteristic to a location associated with evaluation causes at least one validation action, including at least one of:
- validation of data in the non-image data;
- identification of discrepancies between characteristics detected in the image data and indicated in the non-image data;
- adding the medical imaging study to a quality assurance workflow; or
- adding the medical imaging study to a second read workflow.

21. The machine-readable storage medium of claim 16, wherein communicating the identified particular characteristic to a location associated with evaluation causes at least one corrective action, including at least one of:
- performing corrective actions to the non-image data; or
- performing corrective actions to a report associated with the medical imaging study.

22. The machine-readable storage medium of claim 16, wherein communicating the identified particular characteristic to a location associated with evaluation causes at least one display action, including at least one of:
- providing an indication of the identified particular characteristic to an evaluator of the medical imaging study;
- changing a display of the image data at a display of an evaluator of the medical imaging study; or
- changing a report prepared at a display of an evaluator of the medical imaging study.

23. A computing system, comprising:
- a processor; and
- a memory device comprising instructions stored thereon, which when executed by the processor, configure the processor to perform electronic operations with the computing system comprising:
  - obtaining image data and non-image data associated with a medical imaging study for a human subject;
  - using at least one trained artificial intelligence (AI) model to analyze the image data, wherein the trained AI model is validated with a defined governance standard to identify at least one particular characteristic;
  - identifying the particular characteristic in the image data, based on output from the trained AI model, wherein the identified particular characteristic is not indicated by the non-image data; and
  - communicating the identified particular characteristic to a location associated with evaluation of the medical imaging study, wherein the identified particular characteristic controls at least one automated medical image data processing action at the location associated with evaluation.

24. The computing system of claim 23,
- wherein the defined governance standard establishes a specificity and sensitivity to identify the particular characteristic within multiple medical imaging studies performed for multiple human subjects,
- wherein the trained AI model is validated based on a verified identification of the particular characteristic, using a comparison of results identified by natural language processing in study reports and results identified by the trained AI model, the study reports and results being performed on the multiple medical imaging studies performed for the multiple human subjects.

25. The computing system of claim 23, the processor further to perform electronic operations comprising:
- receiving report data provided from evaluation of the medical imaging study;
- using at least one AI model, trained for analysis of natural language processing, to analyze the report data;
- identifying the particular characteristic in the report data, based on output from the AI model trained for analysis of natural language processing; and
- determining at least one evaluation action based on the identifying of the particular characteristic from the report data and the identifying of the particular characteristic from the image data.

\* \* \* \* \*